(12) United States Patent
Yamashita

(10) Patent No.: US 7,129,047 B2
(45) Date of Patent: Oct. 31, 2006

(54) METHOD FOR MANUFACTURING A NUCLEOTIDE DETECTOR

(75) Inventor: Ichiro Yamashita, Nara (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 503 days.

(21) Appl. No.: 10/628,840

(22) Filed: Jul. 28, 2003

(65) Prior Publication Data
US 2004/0018548 A1 Jan. 29, 2004

Related U.S. Application Data

(62) Division of application No. 09/979,438, filed as application No. PCT/JP01/02083 on Mar. 15, 2001, now abandoned.

(30) Foreign Application Priority Data

Mar. 16, 2000 (JP) ............... 2000-73805
Mar. 27, 2000 (JP) ............... 2000-86116

(51) Int. Cl.
C12Q 1/68 (2006.01)
C12M 1/36 (2006.01)
C07H 21/04 (2006.01)
G01N 15/06 (2006.01)

(52) U.S. Cl. ............. 435/6; 435/283.1; 435/287.2; 422/68.1; 536/23.1

(58) Field of Classification Search ............... None
See application file for complete search history.

(56) References Cited

U.S. PATENT DOCUMENTS

| | | |
|---|---|---|
| 4,779,562 A | 10/1988 | Ono |
| 5,959,098 A | 9/1999 | Goldberg et al. |
| 6,183,970 B1 | 2/2001 | Okano et al. |
| 6,239,255 B1 * | 5/2001 | Furlong et al. ............ 530/327 |

FOREIGN PATENT DOCUMENTS

| | | |
|---|---|---|
| EP | 0 881 691 A2 | 12/1998 |
| JP | 62183882 | 8/1987 |
| JP | 62-247860 | 10/1987 |
| JP | 8-155379 | 6/1996 |

(Continued)

OTHER PUBLICATIONS

Science magazine article, vol. 281, pp. 2016-2018, "Quantum Dot Bioconjugates for ultrasensitive Nonisotopic Detection", Warren C.W. Chan and Shuming Nie 1998.

(Continued)

Primary Examiner—BJ Forman
(74) Attorney, Agent, or Firm—Harness, Dickey & Pierce, P.L.C.

(57) ABSTRACT

A nucleotide detector 10 includes: metal particles 12 having a size of the order of nanometers (diameter: about 6 nm) placed on a surface of a substrate 11 at high density with high precision (with spaces of about 12 nm between adjacent particles); and single-stranded DNAs (thiol DNAs) 13 having sulfur atoms at ends bonded to the gold particles 12. The thiol DNAs 13 are placed uniformly over the entire substrate 11 at high density with high precision. Therefore, once a fluorescence-labeled single-stranded DNA is hybridized with any of the thiol DNAs 13, high fluorescence intensity is stably obtained. This detector is therefore usable as a high-performance DNA sensor with a high SN ratio.

12 Claims, 15 Drawing Sheets

FOREIGN PATENT DOCUMENTS

| | | |
|---|---|---|
| JP | 8-229474 | 9/1996 |
| JP | 8-234450 | 9/1996 |
| JP | 11-45990 | 2/1999 |
| JP | 2001181842 | 7/2001 |
| WO | WO 91/02704 | 3/1991 |
| WO | WO 98/04740 | 2/1998 |
| WO | WO 00/29617 | 5/2000 |
| WO | 01/00876 | 1/2001 |

OTHER PUBLICATIONS

Eiki Adachi, "Formation of Holoferritin Hexagonal Arrays in Secondary Films Due to Alder-Type Transition"; Langmuir (1996); vol. 12, No. 7, pp. 1836 to 1839.

English Translation of International Search Report—PCT/JP01/02083; Jun. 26, 2001.

H. Yoshimura; "Two-Dimensional Crystals of Apoferritin"; Adv. Biophys.; vol. 34; pp. 93-107; 1997.

* cited by examiner

METHOD FOR MANUFACTURING A NUCLEOTIDE DETECTOR

TECHNICAL FIELD

The present invention relates to a technology for using a film made of particulates placed with high precision, and more particularly, to a technology used suitably for manufacture of a nucleotide detector and the like.

BACKGROUND ART

First Prior Art

Presently, thanks to the international human genome project and efforts of researchers involved in the project, it is definite that the genome DNA sequence of the human species will be completely clarified in coming several years. However, the genome DNA sequence (base sequence (gene arrangement)) concerned is a genome DMA sequence of a specific person, and not that of an individual. The genome DNA sequence of an individual is slightly different from that of the specific person, where substitution, deletion, insertion, and the like of a base may have occurred in a gene. Normally, such a slight difference is not critical and does not cause any trouble in the life of the individual.

However, it has also been clarified that the difference in genome DNA sequence as described above determines the predisposition of an individual. For example, this difference causes predispositions of individuals such as those who are tolerant to alcohol, those who do not mind the heat, and those who have a low body temperature.

In particular, it is recognized that reaction of the body against a drug differs among individuals, and for this reason, the difference in genome DNA sequence as described above is considered as significantly important information from the standpoint of medical treatment. Therefore, it is strongly desired that the difference in DNA sequence among individuals as described above be detected after the coming determination of the DNA sequences of all the human genes by the human genome project. If genetic information on an individual is made available, it is possible to provide medical treatment optimal for the individual.

To detect the slight difference in genome DNA as described above, a conventional DNA base sequence determination method by use of electrophorasis may be employed. However, this method requires an exceedingly long time and therefore is not practical as a method for detecting genetic information on many subjects.

In addition, it has been discovered that for predispositions prone to genetic diseases and cancers, for example, only a slight difference in base sequence (difference of one base pair, for example) has a critical indication. For example, it has been discovered that sickle cell anemia, which is a lethal genetic disease, is caused by mutation of only one base pair. From this point, also, it is clear that the conventional determination method is not practical.

The basics in detection of the DNA sequence of a gene of an individual are that the DNA sequence of a target gene has been determined and that how the gene of the individual is different from the so-called human gene DNA sequence is sought, as in the instance of sickle cell anemia described above.

As a method capable of detecting the above difference in a short time, a technique using a DNA chip has been proposed, and the effectiveness thereof has been presented.

For example, first, 1000 types of single-stranded DNAs slightly different from the human gene DNA sequence (base sequence) are synthesized in advance, and placed on a substrate. One type of DNA is placed on one section of the substrate, and the position is recorded.

Next, DNA of the subject is taken, and the double helix structure of the DNA is released into single-stranded DNAs. The DNA is then cut into pieces of an appropriate length, and the DNA pieces are fluorescence-labeled.

Subsequently, the fluorescence-labeled DNAs are allowed to hybridize (conjugate) with the single-stranded DNAs placed in advance on the substrate.

After excess DNA and fluorescent dye are washed away, any position/section of the substrate that emits fluorescence is detected. The DNA placed in advance in the section that emits fluorescence is determined to be the DNA sequence that has hybridized with the DNA of the subject. In other words, by detecting the position emitting fluorescence, it is clarified in a short time how the DNA sequence of the subject has mutated from the human gene DNA sequence.

In the technique described above, it is comparatively easy to increase the number of types of single-stranded DNAs placed in advance on the substrate to more than 1000. However, in this case, to attain precise testing, 1000 types or more of single-stranded DNAs must be placed on extremely fine sections of a chip allocated for the respective types of DNAs at high and uniform density so that each section has a uniform amount of DNAs. In particular, in the case that the area of the section allocated for each type of single-stranded DNA becomes finer with increase of the number of types of single-stranded DNAs to be placed, it will become necessary to realize the requirement described above by manipulating a trace amount of single-stranded DNAs.

Second Prior Art

Particulates have a large ratio of the surface area to the volume, and therefore exhibit behaviors generally different from materials that are small in this ratio. For example, particulates of an inorganic material such as titanium oxide and zinc oxide have ultraviolet removal function, antimicrobial function, catalytic function, and the like. Among particulates of an inorganic material, those having a diameter of the order of nanometers (ultra-fine particles) are expected to provide a quantum effect.

Such particulates having the above functions have received attention for their use in the industrial field. In particular, as for ultra-fine particles having a diameter of the order of nanometers, it is urgently required to develop a technique for manufacturing devices using the quantum effect in the industrial scale.

Particulates of protein having a diameter of about 10 to 20 nm have received attention for their use for biosensors and the like. In particular, among a variety of protein particles, there exist particles capable of containing an inorganic material inside. Such protein particles are provided with natures of both the inorganic material and the protein particles.

The particulates described above are normally available in the form of a colloid solution. However, the form of a colloid solution is disadvantageous when the functions of the particulates are to be effectively used. Therefore, search has been made for a technique that permits effective use of the functions of the particulates in the industrial field using the colloid solution as a raw material.

At present, as such a technique permitting effective use in the industrial field, placing the particulates on a substrate is considered most effective. Therefore, desired is establishment of a technique in which an idealistic two-dimensional film made of particulates placed regularly at high density can be easily formed on a substrate.

Various techniques have been proposed so far for placing particulates on a substrate. Some of such techniques handling comparatively large particles have even been commercialized.

For example, Nagayama et al. have disclosed the following method in "Formation of Holoferritin Hexagonal Arrays in Secondary Films Due To Alder-Type Transition", Lanbgmuir 1996, vol. 12, pp. 1836–1839. That is, as shown in FIG. 18, a substrate 11 is put in a solution 18 containing particulates 15 (polystyrene spheres having a diameter of about 1 to 2 μm) dispersed therein, and then gradually lifted in the position vertical to the liquid level, forming a wet film 19 on both surfaces of the substrate 11. In this way, a film made of polystyrene spheres having a diameter of about 1 to 2 μm is formed on the surfaces of the substrate 11.

However, when it is intended to apply the above method to ultra-fine particles having a diameter of about 10 nm, the substrate 11 must be lifted at a very low rate. It is difficult to keep the lifting rate constant when the rate is low. In addition, the array of ultra-fine particles of the film may possibly lose uniformity due to vibration and the like that may be generated during lifting of the substrate 11. For these reasons, it is difficult to apply the above method to ultra-fine particles. To solve this problem, Nagayama et al. disclose a method for forming a two-dimensional crystal film made of protein (ferritin, diameter: about 12 nm). This method will be described with reference to FIG. 16.

FIG. 16 is a view illustrating the method for forming a two-dimensional crystal film made of ferritin. Referring to FIG. 16, first, a platinum blade 21 is placed in the position vertical to the surface of a substrate 11 that is mounted on a base 20. A liquid 16 containing ferritin dispersed therein is then dropped into a small space between the substrate 11 and the blade 21, so that the liquid 16 is held in and around the space (hatched portion in FIG. 16) due to the surface tension of the liquid 16. Thereafter, while the blade 21 is kept fixed, the base 20 (that is, the substrate 11) is moved in the direction shown by the arrow at a constant speed (2 μm/sec. in this case). This results in the liquid 16 being applied to the substrate 11. The water content of the liquid 16 is evaporated gradually as the liquid 16 is sequentially applied to the substrate 11, allowing formation of a thin film 22 made of ferritin. The thin film 22 has a thickness of about 10 layers of ferritin particles.

Problems to be Solved

If the above requirement described in relation with the first prior art fails to be realized, the DNA chip causes various problems. To state specifically, if the density of DNAs placed in a certain section is too low, the intensity of fluorescence emitted from hybridized DNAs decreases, deteriorating the signal to noise (SN) ratio. In other words, the fluorescence from hybridized DNAs may possibly be buried in background fluorescence inevitably generated.

Moreover, if the absolute amount of DNAs placed varies with the sections, a plurality of sections may emit fluorescence at different intensities when the DNA of the subject hybridizes in two or more sections. In this event, it is unknown why the fluorescence intensity is low in one section compared with that in another section. Specifically, it is difficult to determine whether the fluorescence intensity is low because the absolute amount of DNA placed is small or because the absolute amount DNA placed is so large that emission of fluorescence is allowed despite of weak non-specific adsorption. This may results in mistake of the determination. Furthermore, the variation in the absolute amount of DNAs placed among chips indicates that the reproducibility of the chip quality is poor. This may results in generation of defective DNA chips.

To overcome the above problems, it is necessary to place types of DNAs on the substrate at high density (about $10^{12}$ pcs./cm$^2$) by a uniform amount for each type.

As for the second prior art, in order to realize uniform-quality particulate films with high reproducibility by use of the technique disclosed by Nagayama et al., it is necessary to ensure the movement of the base 20 (that is, the substrate 11) while maintaining a constant ultra-low speed of 2 μm/sec. However, in this movement maintaining a constant ultra-low speed, the speed tends to be greatly influenced by a subtle variation in the environment. For example, the moving speed changes with a slight vibration in the environment. A fluctuation in an atmosphere (such as wind and operator's respiration) changes the amount of evaporation of the ferritin solution. By these changes, the reproducibility of the quality of the particulate films deteriorates. It is therefore necessary to provide a means for ensuring the movement of the base 20 while maintaining a constant ultra-low speed and a means for keeping the surrounding atmosphere constant. However, it is not easy to actually provide these means. Therefore, the method disclosed by Nagayama et al. finds difficulty in providing particulate films with a uniform quality, and thus is not suitable for applications to formation of a particulate film over a large-area substrate and to mass production of particulate films.

In addition, using a large-size blade 21 made of platinum costs high. However, if the blade 21 is made of a material other than platinum, it may possibly be corroded. Moreover, it is very difficult to produce a large-size rigid blade having nanometer-order surface precision.

Other methods have also been proposed, including a method in which a substrate surface is treated in various ways and a particulate film prepared in advance is transferred to the substrate surface (Japanese Laid-Open Patent Publication No. 8-155379), a method in which amphiphilic molecules such as casein molecules are used as a binder and a particulate thin film is automatically formed on the binder (Japanese Laid-Open Patent Publication No. 8-229474), and a lithographic method using a particulate film as a substrate (Japanese Laid-Open Patent Publication No. 8-234450). However, all of these methods are not suitable for mass production.

DISCLOSURE OF THE INVENTION

An object of the present invention is to provide a nucleotide detector capable of detecting target nucleotide (DNA, RNA, or the like) with high precision.

Another object of the present invention is to provide a method for easily producing a two-dimensional crystal film made of particulates of protein or the like having a diameter of the order of nanometers arranged at high density and at desired positions with high precision.

The nucleotide detector of the present invention includes: a substrate; metal particles placed regularly on the substrate; and one of a pair of nucleotide molecules capable of conjugating with each other, the one nucleotide molecule being bonded to each of the metal particles.

Either one of a pair of nucleotide molecules capable of conjugating with each other is bonded to each of the metal particles placed regularly on the substrate. Therefore, the conjugation between the one nucleotide molecule and the other nucleotide molecule capable of conjugating with the former can be established in uniform over the substrate.

Thus, when the other nucleotide molecule is made detectable with a fluorescent label or the like, for example, a stable detection signal can be obtained.

The method for manufacturing a nucleotide detector of the present invention includes the steps of: (a) arranging complex particles each including a metal particle and a protein molecule holding the metal particle on a substrate; (b) removing the protein molecules; and (c) bonding one of a pair of nucleotide molecules capable of conjugating with each other to each of the metal particles left on the substrate in the step (b).

By placing the complex particles on the substrate and removing the protein molecules, only metal particles regularly placed are left on the substrate. To each of these metal particles, bonded is one of a pair of nucleotide molecules capable of conjugating with each other. In this way, attained is a nucleotide detector in which nucleotide molecules constituting one of a pair of nucleotide molecules capable of conjugating with each other are regularly placed on the substrate.

The protein molecules may be Dps protein or apoferritin.

The nucleotide molecules may be a plurality of types of nucleotide molecules having different base sequences.

The method for producing a particulate film of the present invention includes the steps of: (a) placing a substrate in a container so that a surface of the substrate is vertical to the liquid level of a liquid containing particulates filled in the container; and (b) raising or lowering the liquid level of the liquid.

According to the method for producing a particulate film of the present invention, by gradually raising or lowering the level of the liquid, the liquid level slightly rises along the substrate at the interface between the liquid and the substrate, forming a meniscus portion. Since the meniscus portion has a large surface area, a dispersion medium of the liquid evaporates, resulting in reduction of the amount of the dispersion medium in the meniscus portion. This causes an effect similar to the micro-capillary effect in the meniscus portion, where the liquid flows toward this portion. As a result, the particles exist in the meniscus portion of the liquid in a significantly high concentration, and thus are arranged on the surface of the substrate at high density with high precision. In other words, a film of particulates arranged at high density with high precision is formed on the surface of the substrate.

The method for producing a particulate film of the present invention is particularly preferable when the particulates have a diameter of 50 nm or less.

The particulates may be protein.

The protein may contain an inorganic material inside.

The concentration of the protein in the liquid is preferably 10 μg/ml to 500 mg/ml.

The liquid may contain an electrolyte.

Preferably, a liquid level raising or lowering rate of the liquid is substantially constant, and it is 10 mm/min. or less.

The liquid may be allowed to flow out by gravity.

The substrate may have a convex and concave pattern on a surface.

BEST MODE FOR CARRYING OUT THE INVENTION

Hereinafter, embodiments of the present invention will be described with reference to the relevant drawings. Note that nucleotides such as DNAs and RNAs as used herein are single-stranded unless otherwise specified.

Embodiment 1

First, the construction of a nucleotide detector of this embodiment will be described.

Figure 1:
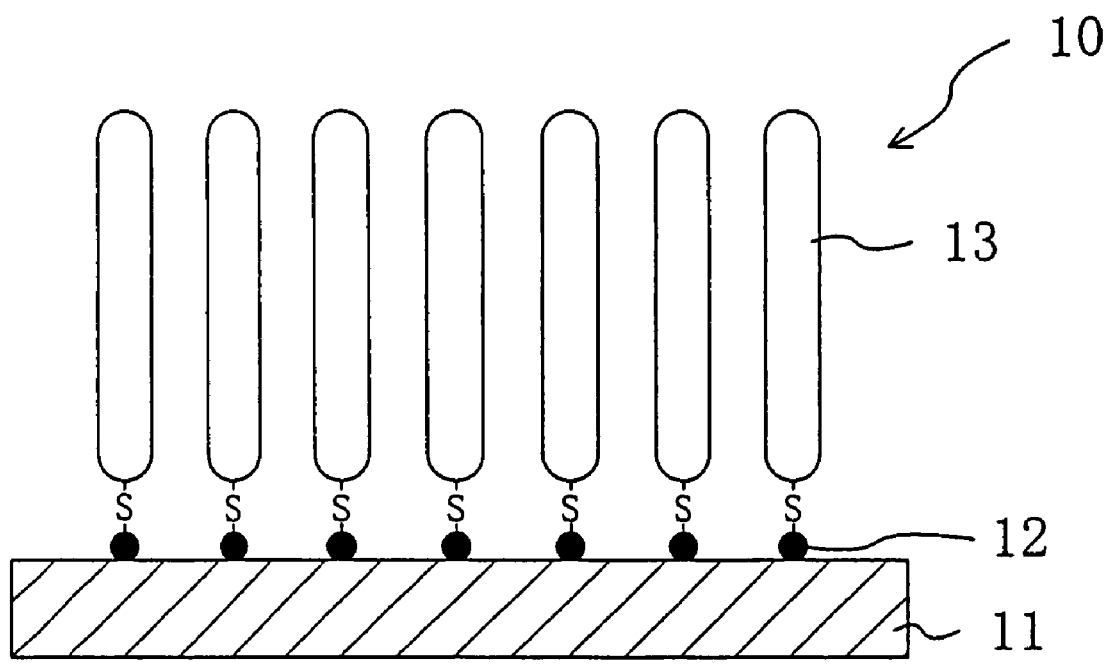
FIG. 1 is a diagrammatic illustration of a nucleotide detector of the present invention.

As shown in FIG. 1, a nucleotide detector 10 of this embodiment is a DNA sensor, which includes a substrate 11, gold particles 12 having a size of the order of nanometers (diameter of about 6 nm) placed on a surface of the substrate 11 at high density with high precision (with spaces of about 12 nm between adjacent particles), and single-stranded DNAs (thiol DNAs) 13 each having a sulfur atom at an end. The thiol DNAs 13 are bonded to the gold particles 12.

A method for manufacturing the nucleotide detector 10 of this embodiment will be described with reference to the relevant drawings. For fabrication of the nucleotide detector 10 of this embodiment, it is necessary to place the gold particles 12 having a diameter of about 6 nm on a surface of the substrate 11 at high density with high precision. In other words, it is necessary to arrange and immobilize the gold particles 12 two-dimensionally on a surface of the substrate 11.

Figure 2A:
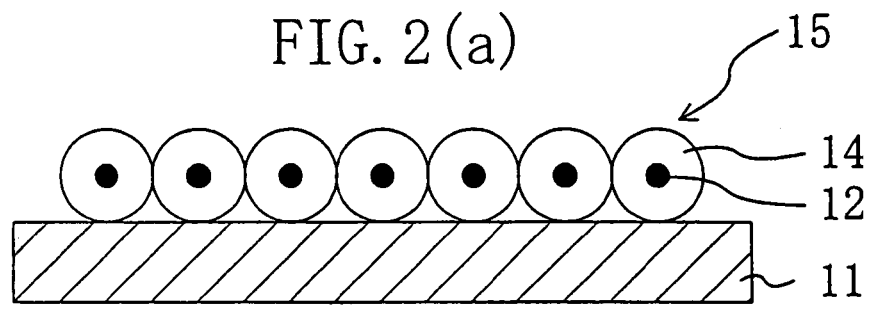
FIG. 2 diagrammatically illustrates a method for manufacturing the nucleotide detector of the present invention.

First, in a step shown in FIG. 2(a), complex particles 15 each composed of a protein molecule 14 holding the gold particle 12 are prepared and placed on the surface of the substrate 11, to thereby form a complex film in which the complex particles 15 are placed on the surface of the substrate 11 at high density with high precision.

Figure 2B:
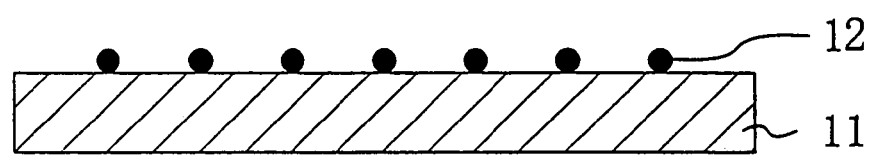

In a step shown in FIG. 2(b), the protein molecules 14 are removed from the complex particles 15, to leave only the gold particles 12 behind.

Figure 2C:
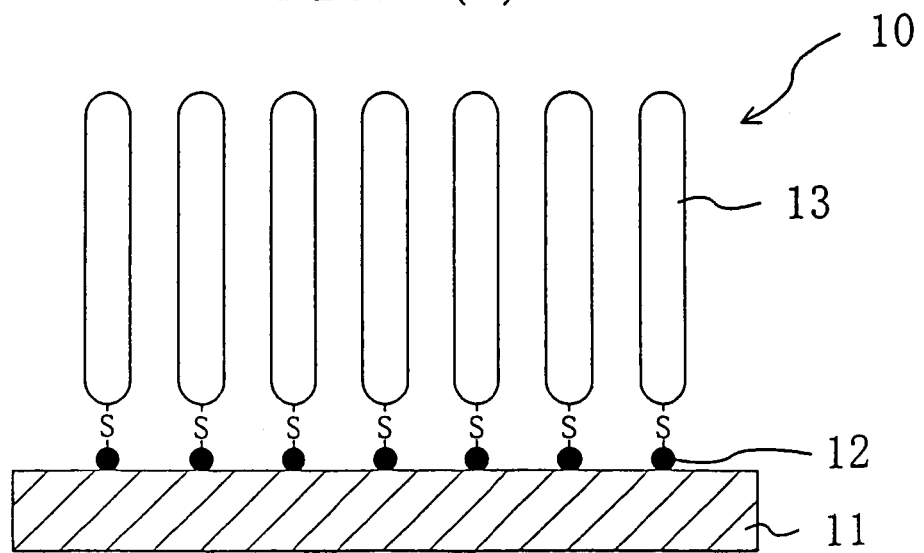

In a step shown in FIG. 2(c), the thiol DNAs 13 are bonded to the gold particles 12.

The step shown in FIG. 2(a) will be described in more detail.

Figure 3:
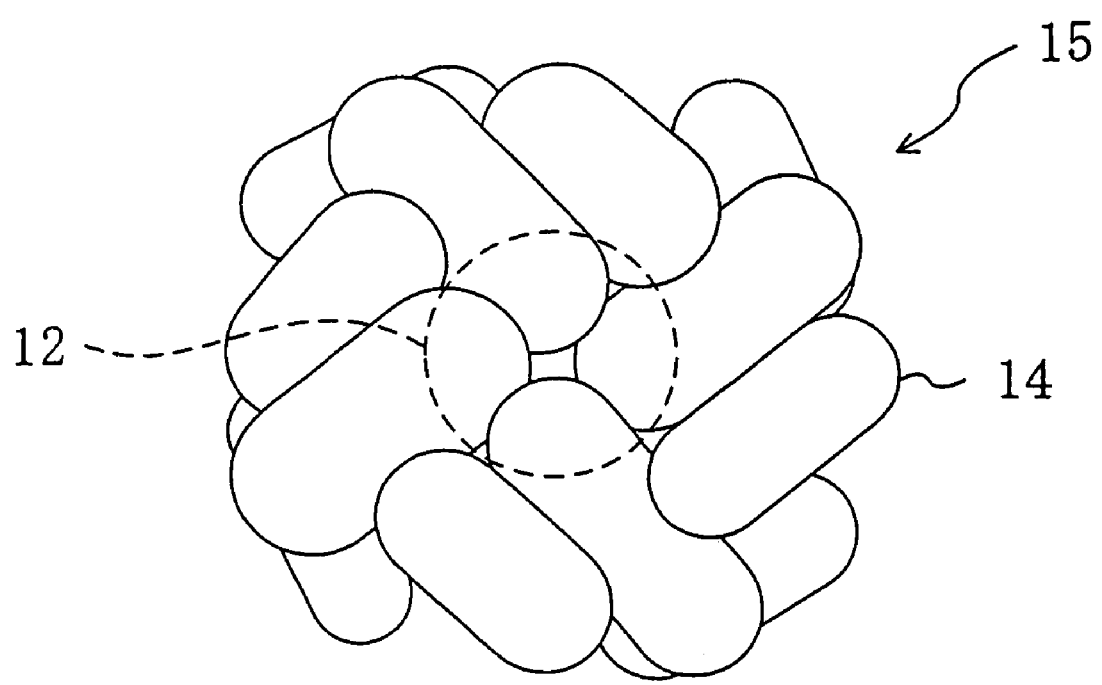
FIG. 3 is a diagrammatic illustration of a structure of a complex particle.

As shown in FIG. 3, the complex particle 15 used in this embodiment is a gold-protein complex where the protein molecules 14 surround the gold particle 12 to hold the gold particle 12 inside. As the protein molecules 14 of the complex particle 14, used is apoferritin derived from ferritin extracted from organs such as spleens and livers of horses, cows, and other animals. The protein molecules 14 are not limited to this, but other proteins capable of holding metal particles, such as Dps protein, can also be used suitably.

Apoferritin used in this embodiment is a protein of 24 subunits of molecular weight of about 20,000 having an outer diameter of the entire 24 subunits of about 12 nm, which generally exists as ferritin in an organ. Ferritin is a complex between the apoferritin and about 3000 molecules of ferric oxide ($Fe_2O_3$).

Apoferritin has a nature of holding metal particles, and therefore can be made to hold the gold particles 12 by use of a solution of $KAuCl_4$ or $HAuCl_4$ (concentration: about 1 to 5 mM), for example. Hereinafter, a method for making apoferritin hold the gold particles 12 using this solution will be described.

$AuCl_4^-$ is present in the $KAuCl_4$ or $HAuCl_4$ solution. By reducing $AuCl_4^-$, gold particles are formed. Using this nature, the gold particles 12 can be produced by putting a protein that generally has reducing nature in the $HAuCl_4$ solution.

However, in the case of using apoferritin as the protein, $AuCl_4^-$ fails to enter apoferritin the inside of which is negatively charged. To overcome this problem, amino acid residues located inside the apoferritin are genetically changed by substitution so that the inside of apoferritin is positively charged. By this operation, $AuC_4^-$ is allowed to enter the apoferritin and is reduced inside to produce the gold particle 12. Gold particles are also produced outside the apoferritin. Such gold particles produced outside can be separated by centrifugation.

As a result of the above operation, apoferritin particles containing the gold particles 12 inside are attained.

Hereinafter, discussed is a method for placing the complex particles 15 on a surface of the substrate 11 at high density with high precision, in other words, a method for arranging and immobilizing the complex particles 15 two-dimensionally on a surface of the substrate 11. In this embodiment, either of methods 1 to 5 described below may be employed. Note that all of methods 1 to 5 use apoferritin particles containing the gold particles 12 inside as the complex particles 15.

Method 1

As method 1, a method disclosed in Japanese Laid-Open Patent Publication No.11-45990 will be described with reference to FIG. 4.

Figure 4A:
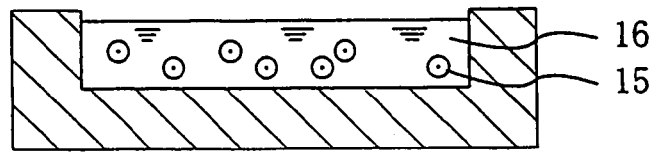
FIG. 4 illustrates a method for arranging and immobilizing complex particles two-dimensionally on a substrate.

First, referring to FIG. 4(a), prepared is a liquid 16 with the complex particles 15 dispersed therein (in this embodiment, a mixture of a phosphoric acid buffer solution, pH 5.3, having a concentration of 40 mM and a sodium chloride aqueous solution having a concentration of 40 mM in equal proportions, with apoferritin particles containing the gold particles 12 inside dispersed therein).

Figure 4B:
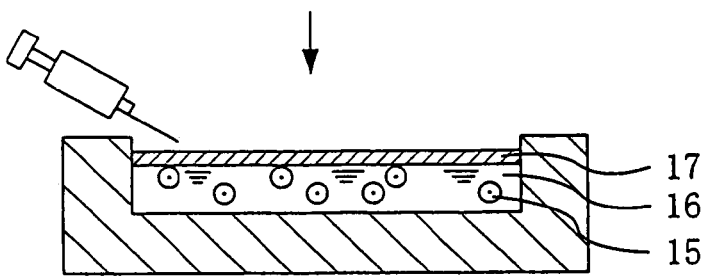

Referring to FIG. 4(b), poly-1-benzil-1-histidine (PBLH) is gently injected to float on the surface of the liquid 16 with a syringe or the like, to thereby form a polypeptide film 17 made of PBLH on the surface of the liquid 16. The pH of the liquid 16 is then adjusted.

Figure 4C:
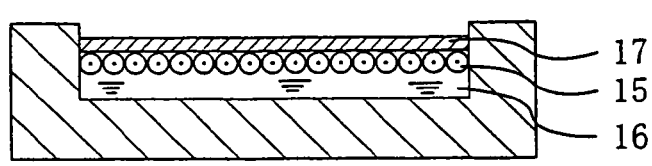

Referring to FIG. 4(c), an increasing amount of the complex particles 15 come to attach to the polypeptide film 17 with the lapse of time, to finally form two-dimensional crystal of the complex particles 15. This is because while the polypeptide film 17 is positively charged, the complex particles 15 are negatively charged.

Figure 4D:
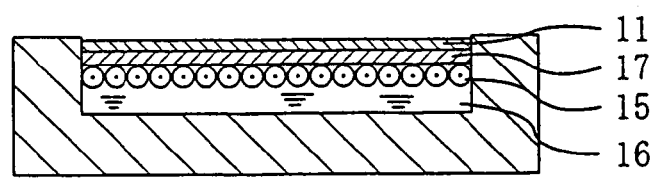

Referring to FIG. 4(d), the substrate 11 is mounted (floated) on the polypeptide film 17, to allow the polypeptide film 17 to attach to the substrate 11.

Figure 4E:
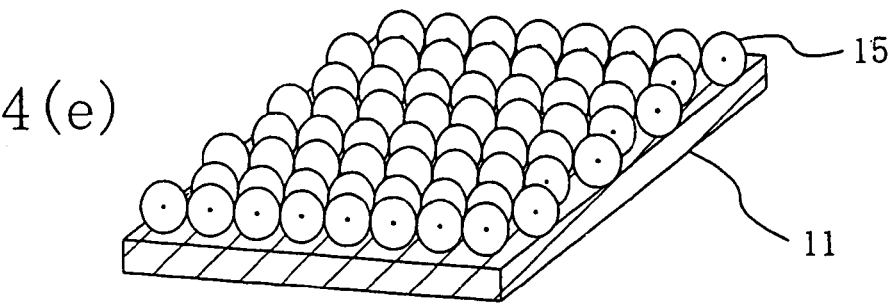

Referring to FIG. 4(e), the substrate 11 is taken out, to thereby obtain the substrate 11 with two-dimensional crystal of the complex particles 15 attaching thereto via the polypeptide film 17.

Method 2

Method 2 is the same as the technique by Nagayama et al. disclosed in "Formation of Holoferritin Hexagonal Arrays in Secondary Films Due To Alder-Type Transition", Lanbgmuir 1996, vol. 12, pp. 1836–1839, described above in the second prior art (see FIG. 15).

Figure 15:
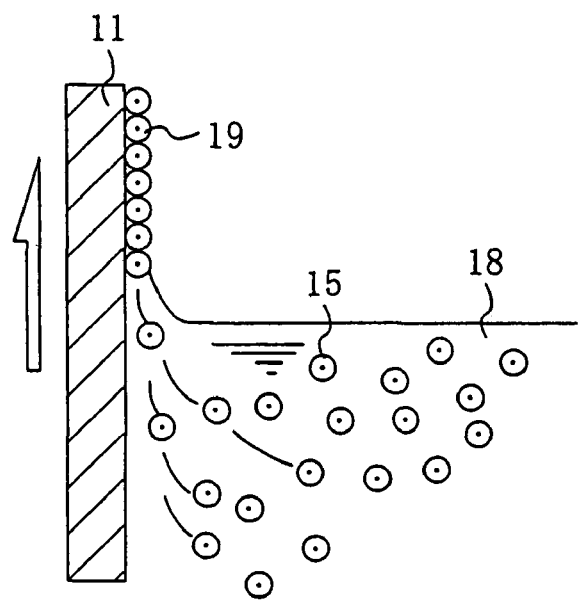
FIG. 15 is an illustration of a conventional method for placing particles on a substrate.

First, the complex particles 15 are dispersed in a solution 18 (pure water, pure water with an electrolytic substance such as sodium chloride added thereto, or the like). Thereafter, as shown in FIG. 15, the substrate 11 is put in the solution 18. The substrate 11 is then gradually lifted while the surface of the substrate 11 is held vertical to the liquid level. This forms a wet film 19 containing the complex particles 15 dispersed two-dimensionally on both surfaces of the substrate 11. Once the wet film 19 is dried, obtained is the substrate 11 with two-dimensional crystal of the complex particles 15 attaching to both surfaces thereof.

Method 3

Method 3 is the same as the other technique by Nagayama et al. described above in the second prior art (see FIG. 16).

Figure 16:
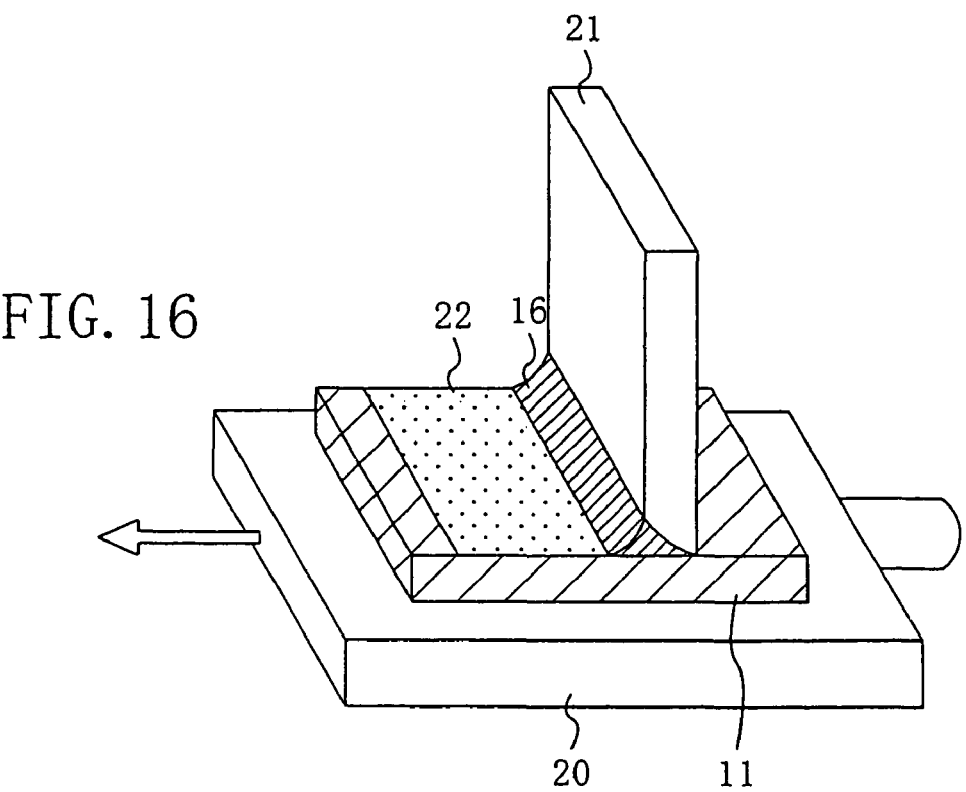
FIG. 16 is an illustration of another conventional method for placing particles on a substrate.

As shown in FIG. 16, the platinum blade 21 is placed vertical to the surface of the substrate 11 that is mounted on the base 20. The liquid 16 containing the complex particles 15 dispersed therein is then dropped in a small space between the substrate 11 and the blade 21, so that the liquid 16 is held in and around the space due to the surface tension of the liquid 16. Thereafter, while the blade 21 is kept fixed, the base 20 (that is, the substrate 11) is gradually moved in the direction indicated by the arrow at a constant rate (2 μm/sec. in this case). This results in formation of a thin film 22 of the liquid 16 on the substrate 11. The thin film 22 includes the complex particles 15 dispersed two-dimensionally. Once the thin film 22 is dried, obtained is the substrate 11 with two-dimensional crystal of the complex particles 15 attaching to one surface thereof. This two-dimensional crystal film of the complex particles 15 has a thickness of about 10 layers of the complex particles 15.

Method 4

As method 4, a method based on a transfer method developed by Yoshimoto et al. (Adv. Biophys., vol. 34, pp. 99–107 (1997)) will be described with reference to FIG. 5.

Figure 5A:
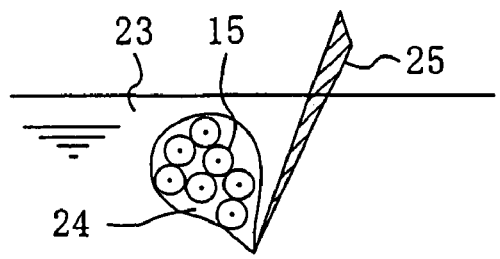
FIG. 5 illustrates another method for arranging and immobilizing complex particles two-dimensionally on a substrate.

In a step shown in FIG. 5(a), a liquid 24 containing the complex particles 14 dispersed therein (a suspension containing ferric oxide-containing apoferritin) are injected into a sucrose solution 23 having a concentration of 2% with a syringe 25.

Figure 5B:
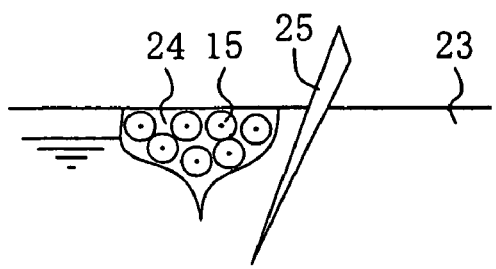

In a step shown in FIG. 5(b), drops of the liquid 24 emerge on the sucrose solution 23.

Figure 5C:
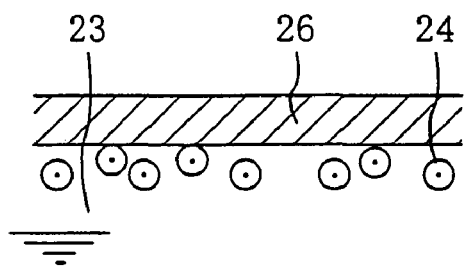

In a step shown in FIG. 5(c), drops of the liquid 24 arriving first at the gas-liquid interface form an amorphous film 26 of apoferritin, and drops of the liquid 24 arriving late attach to the bottom surface of the amorphous film 26.

Figure 5D:
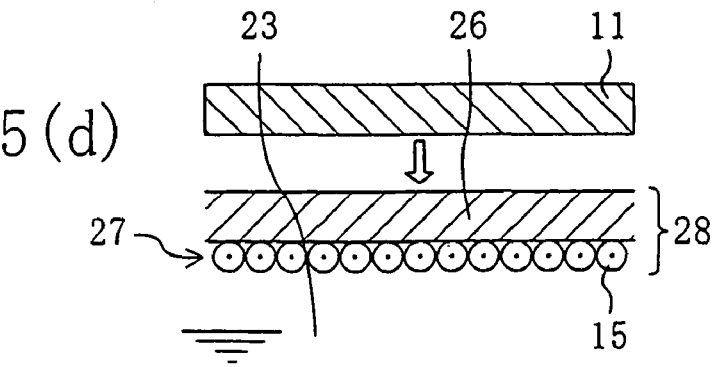

In a step shown in FIG. 5(d), two-dimensional crystal 27 made of the complex particles 15 is formed under the amorphous film 26. Thereafter, the substrate 11 (a silicon wafer, a carbon grid, a glass substrate, and the like) is mounted on a film 28 composed of the amorphous film 26 and the two-dimensional crystal 27 of the complex particles 15. The film 28 made of the complex particles 15 is thus transferred to the surface of the substrate 11.

The surface of the substrate 11 may be subjected to hydrophobic treatment before the transfer, to facilitate the transfer of the film 28 to the surface of the substrate 11. As the hydrophobic treatment of the substrate 11, usable is treatment of the surface with hexamethyldisilazane (HMDS, $(CH_3)_3SiNHSi(CH_3)_3$) or the like when the substrate 11 is a silicon substrate, and coating of the surface with a fluorocarbon monomolecular film when the substrate 11 is a glass substrate, for example.

Method 5

Method 5 will be described with reference to FIG. 6.

Figure 6:
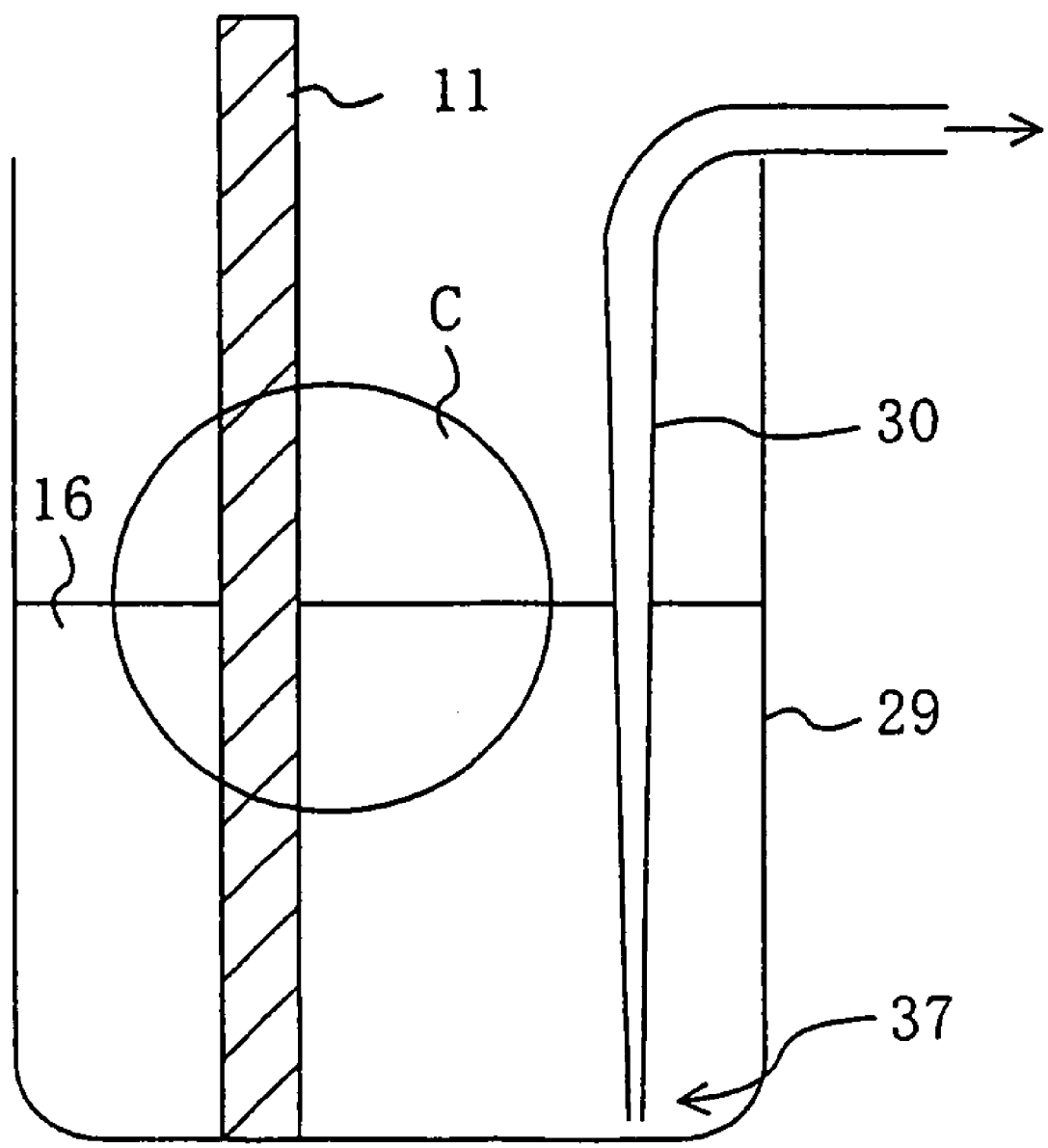
FIG. 6 illustrates yet another method for arranging and immobilizing complex particles two-dimensionally on a substrate.

First, referring to FIG. 6, the substrate 11 is put in a container 29 containing the liquid 16 used in method 1 so that the surface of the substrate 11 is substantially vertical to the level of the liquid 16. The liquid 16 is then gradually drawn out at a constant rate from the container 29 via a tube 30 or the like. Alternatively, as will be described later, a hole may be formed in the lower portion of the container 29 to gradually draw out the liquid 16 at a constant rate.

By the above drawing, a wet film is formed on both surfaces of the substrate 11. This wet film includes the complex particles 15 dispersed two-dimensionally, as the wet film shown in FIG. 2. Therefore, once the wet film is dried, obtained is the substrate 11 with two-dimensional crystal of the complex particles 15 attaching thereto.

Method 5 will be described later in more detail following description of Embodiment 3.

Next, the step shown in FIG. 2(b) will be described in more detail as follows.

Protein molecules are normally susceptible to heat and thus can be removed by applying heat. The protein molecules 14 of the complex particles 15 are therefore removed by heat treatment. For example, the protein molecules 14, and the polypeptide film 17 if method 1 was adopted, are consumed by being left to stand in an atmosphere of inert gas such as nitrogen at 400 to 500° C. for about one hour. As a result, the gold particles 12 are left behind on the substrate 11 in the shape of dots arranged regularly at high density with high precision.

Thus, the gold particles 12 that had been held inside the complex particles 15 are uncovered in the state of a two-dimensional array on the substrate 11 arranged at high density with high precision.

Next, the step shown in FIG. 2(c) will be described in more detail.

The nucleotide detector 10 of this embodiment is constructed of thiol DNAs 13 bonded to the gold particles 12 that are placed on the substrate 11 in the manner described above.

The gold particles 12 and the thiol DNAs 13 can be bonded together by putting the substrate 11 with the gold particles 12 placed thereon in contact with an aqueous solution of the thiol DNAs 13 and leaving to stand for a predetermined period of time. The reason is that since sulfur easily reacts with gold, the sulfur at the end of the thiol DNA or RNA easily conjugates with the gold particle 12.

Specifically, when the thiol DNA 13 in the aqueous solution comes into contact with the gold particle 12 on the substrate 11, the sulfur atom S of the thiol DNA 13 and the gold particle 12 establish one-to-one conjugation as shown in FIG. 2(c). As a result, the thiol DNAs 13 are placed on the substrate 11 at significantly high density with significantly high precision. Since the gold particles 12 are arranged two-dimensionally on the substrate 11 at high density with high precision, the resultant nucleotide detector 10 has the thiol DNAs 13 bonded to the gold particles 12 arranged two-dimensionally on the substrate 11 at high density with high precision, and also has particles placed with a uniform number of particles per unit area determined depending on the size of the particles.

Note that in this step, nucleotides such as thiol RNAs and PCR primers with thiol ends may be used in place of the thiol DNAs 13.

In the above step, the concentration of the thiol DNAs 13 in the aqueous solution may be determined, theoretically, so that the number of the thiol DNAs 13 matches with the number of the gold particles 12 on the substrate 11. Actually, however, it is preferable to set the number of the thiol DNAs 13 greater than the number of the gold particles 12. Therefore, in this embodiment, a high-concentration aqueous solution of thiol DNAs is prepared to ensure that the solution contains the thiol DNAs 13 greater in number than the complex particles 15 contained in the complex-dispersed liquid 16.

As the temperature of the aqueous solution of the thiol DNAs 13 is higher, the bonding of the sulfur atoms S of the thiol DNAs 13 to the gold particles 12 is more facilitated. However, if the temperature is excessively high, handling of the aqueous solution of the thiol DNAs 13 becomes difficult due to intensified convection and the like. Excessively high temperature is also disadvantageous from the standpoint of energy consumption. In normal, therefore, the aqueous solution of the thiol DNAs 13 is preferably warmed to about 20 to 60° C.

Thus, the nucleotide detector 10 of this embodiment capable of easily detecting DNA or RNA of which detection is desired is attained.

Next, a DNA detecting method using the nucleotide detector 10 as the DNA sensor will be described.

First, a solution containing a group of DNAs for detection (subject DNA group) is prepared. The DNAs in the subject DNA group are labeled with fluorescence in advance.

The solution of the fluorescence-labeled subject DNA group is put in contact with the nucleotide detector 10 with the thiol DNAs placed thereon and left to stand in this state.

After the lapse of a certain period of time, if there exists a DNA in the subject DNA group that hybridizes with the thiol DNA of the nucleotide detector 10, the thiol DNA of the nucleotide detector 10 and the DNA in question in the subject DNA group constitute a double helix, establishing stable bonding.

The resultant nucleotide detector 10 is washed with a solution such as water containing no fluorescent substance, to remove the remaining DNAs in the subject DNA group that have not bonded to the thiol DNAs of the nucleotide detector, together with a slight amount of the fluorescent substance left behind on the nucleotide detector 10.

Thereafter, the surface of the nucleotide detector 10 is irradiated with light such as laser light to observe fluorescence. During this observation, fluorescence is emitted if the subject DNA group includes a DNA having a sequence that hybridizes with the thiol DNA of the nucleotide detector 10.

Thus, as described above, whether or not a DNA having a predetermined sequence exists in the subject DNA group can be detected by examining whether or not fluorescence is emitted.

In particular, the nucleotide detector 10 of this embodiment has thiol DNAs placed in uniform over the substrate at high density with high precision. Therefore, this nucleotide detector can be used as a high-performance DNA sensor that provides fluorescence at high intensity in uniform with high precision and is significantly high in SN ratio. Therefore, by using the nucleotide detector 10 of this embodiment as the DNA sensor, it is possible to determine that a DNA having a predetermined sequence exists in the subject DNA group if the detected fluorescence intensity is higher than a predetermined value. In other words, it is possible to substantially eliminate the possibility of erroneous determination on whether or not a DNA having a predetermined sequence exists.

Moreover, the nucleotide detector 10 of this embodiment has thiol DNAs placed in uniform over the substrate at high density with high precision. Therefore, the fluorescence intensity exhibited after hybridization of a DNA having a predetermined sequence hardly differs among substrates. This eliminates the necessity of changing the setting of the threshold value of the fluorescence intensity for each substrate for determination on whether or not a hybridized DNA exists, and thus produces a remarkable effect of widely reducing the trouble for adjusting the fluorescence detector.

In this embodiment, the nucleotide detector 10 was used as the DNA sensor. Alternatively, the nucleotide detector 10 may be used as a RNA sensor by using an RNA group as the subject for detection, in place of the DNA group.

In this embodiment, the gold particles 12 and the thiol DNAs 13 were used. Alternatively, a combination of particles of other metal and DNAs treated to permit bonding to the metal particles may be used, in place of the combination of the gold particles 12 and the thiol DNAs 13.

Conventionally, nucleotide detectors such as DNA chips are not reusable. In the nucleotide detector 10 of this embodiment, DNAs (or RNAs) are fixed to the substrate via sulfur atoms and the gold particles so firmly that this fixation can be maintained even at a temperature of 100° C. Thus, the nucleotide detector of this embodiment can be reused by dissociating the hybridized DNA from the thiol DNA and washing it away.

Embodiment 2

In embodiment 1, detection of one type of DNA was described. In reality, there is an occasion that many types of DNAs are detected simultaneously. In this embodiment, therefore, detection of many types of DNAs simultaneously will be described.

In detection of many types of DNAs, a nucleotide detector capable of detecting many types of DNAs is manufactured by a technique as shown in FIG. 7, for example.

Figure 7A:
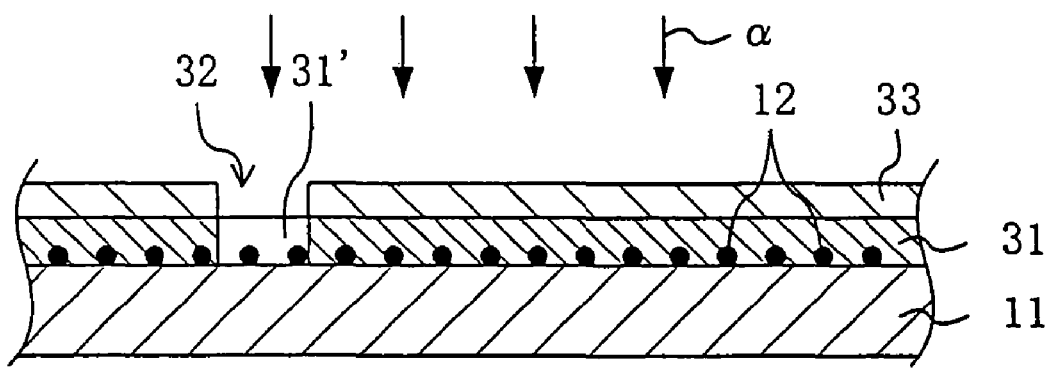
FIG. 7 illustrates a method for fabricating a nucleotide detector capable of detecting various types of DNAs.

First, referring to FIG. 7(a), after the two-dimensional placement of the gold particles 12 on the substrate 11 as in Embodiment 1, a resin resist film 31 that can be denatured with light and removed with a developer is formed on the substrate. Thereafter, a mask 33 having an opening 32 is formed on the resin resist film 31, and the resultant substrate is irradiated with light α incident from above the mask 33. This denatures a portion 31' of the resin resist film 31 located in the opening 32.

Figure 7B:
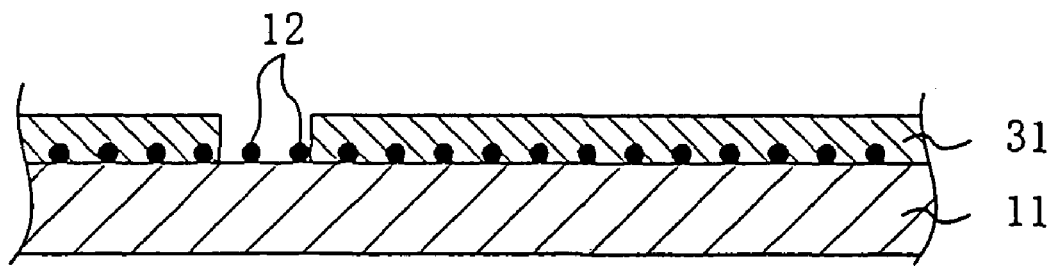

Referring to FIG. 7(b), the resultant substrate is treated with a developer to remove the denatured portion 31' of the resin resist film 31 and thus expose the corresponding gold particles 12 on the substrate 11.

The resultant substrate is then treated with the aqueous solution of the thiol DNAs in a manner as described with reference to FIGS. 2(b) and 2(c). As a result, the thiol DNAs 13 are bonded to only the gold particles in the exposed portion.

The type of the thiol DNAs 13 (in base sequence or the like) to be bonded to the exposed gold particles 12 is changed one after another, and the above operation is repeated for each type, to finally produce a nucleotide detector including DNAs bonded to the substrate in which the sequences of the DNAs are different among sections of the substrate.

By use of the nucleotide detector of this embodiment, it is possible to detect a plurality of different DNAs simultaneously. Detection using the nucleotide detector of this embodiment is performed in the following manner.

First, as in Embodiment 1, a solution of a subject DNA group labeled with fluorescence in advance is put in contact with the nucleotide detector of this embodiment and left to stand in this state.

If there exists a DNA in the subject DNA group that hybridizes with the thiol DNA of the nucleotide detector of this embodiment, the thiol DNA of the nucleotide detector and the DNA in question in the subject DNA group constitute a double helix, providing stable bonding.

The resultant nucleotide detector is washed with water or the like, and irradiated with light to observe fluorescence. During this observation, fluorescence is emitted if a DNA in the subject DNA group has bonded to the thiol DNA of the nucleotide detector of this embodiment. By specifying the position from which fluorescence is emitted, the sequence of the hybridized DNA can be detected.

The nucleotide detector of this embodiment also has thiol DNAs placed in uniform over the entire substrate at high density with high precision. Therefore, this nucleotide detector can be used as a high-performance DNA sensor that provides fluorescence at high intensity in uniform with high precision and is high in SN ratio. In particular, in the nucleotide detector of this embodiment, the thiol DNAs having different sequences among sections are fixed to the substrate by a uniform amount for each section. Therefore, the nucleotide detector of this embodiment can overcome the problem of the conventional DNA sensor that it is difficult to determine whether or not a DNA having a predetermined sequence exists in a section with low fluorescence intensity.

Moreover, in the nucleotide detector of this embodiment, the fluorescence intensity hardly differs among substrates. This eliminates the necessity of changing the setting of the threshold value of the fluorescence intensity for each substrate for determination on whether or not a hybridized DNA exists, and thus produces a remarkable effect of widely reducing the trouble for adjusting the fluorescence detector.

Embodiment 3

In this embodiment, another case of detecting many types of DNAs simultaneously will be described.

Figure 8A:
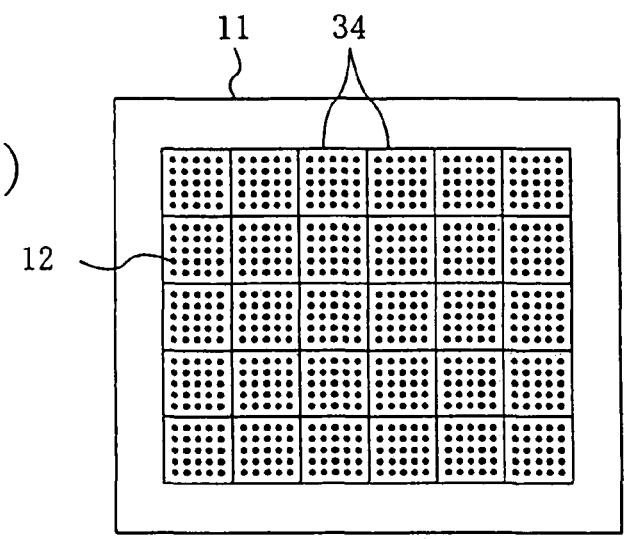
FIG. 8 illustrates another method for fabricating a nucleotide detector capable of detecting various types of DNAs.

1) First, as shown in FIG. 8(a), electrodes 34 are placed in advance on the substrate 11, and the gold particles 12 are placed on the electrodes 34 as in Embodiment 1.

Figure 8B:
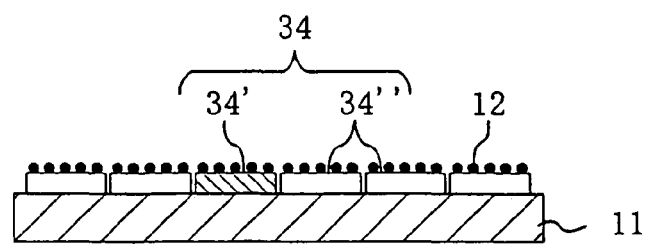
Figure 8C:
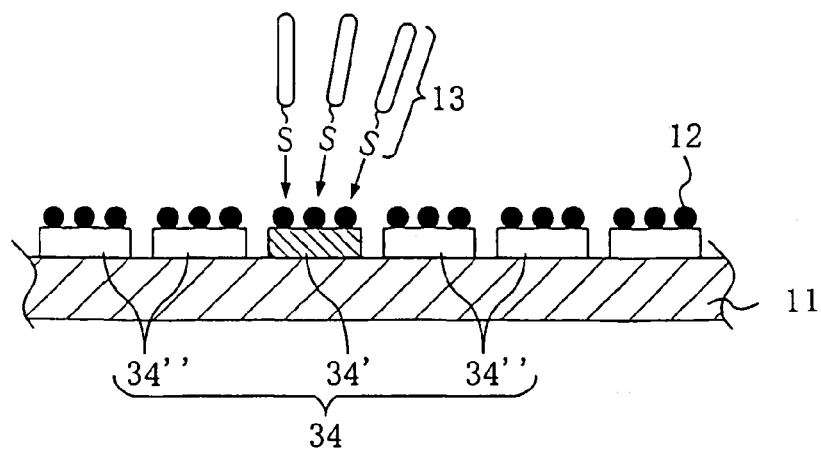

2) As shown in FIG. 8(b), a positive potential is applied to an electrode 34' in a region in which DNAs having a specific sequence are to be placed, and a negative potential is applied to the other electrodes 34".

3) The resultant substrate is put in contact with a solution of the thiol DNAs 13. The thiol DNAs 13, which are negatively charged intensively, are kept away from the electrodes 34" to which a negative potential has been applied, and thus concentrate on the electrode 34' to which a positive potential has been applied. As a result, the thiol DNAs 13 establish one-to-one bonding to the gold particles 12 on the electrode 34'.

The operations 1) to 3) above are repeated changing the type of the thiol DNAs 13 (in base sequence or the like) one after another and also changing the electrode 34' to which the positive potential is applied. In this way, a nucleotide detector including many thiol DNAs having different sequences bonded to one substrate 11 (multi-type DNA sensor) can be manufactured.

The nucleotide detector of this embodiment can be used as a high-performance multi-type DNA sensor as in Embodiment 2.

Detailed Description of Method 5

Figure 9:
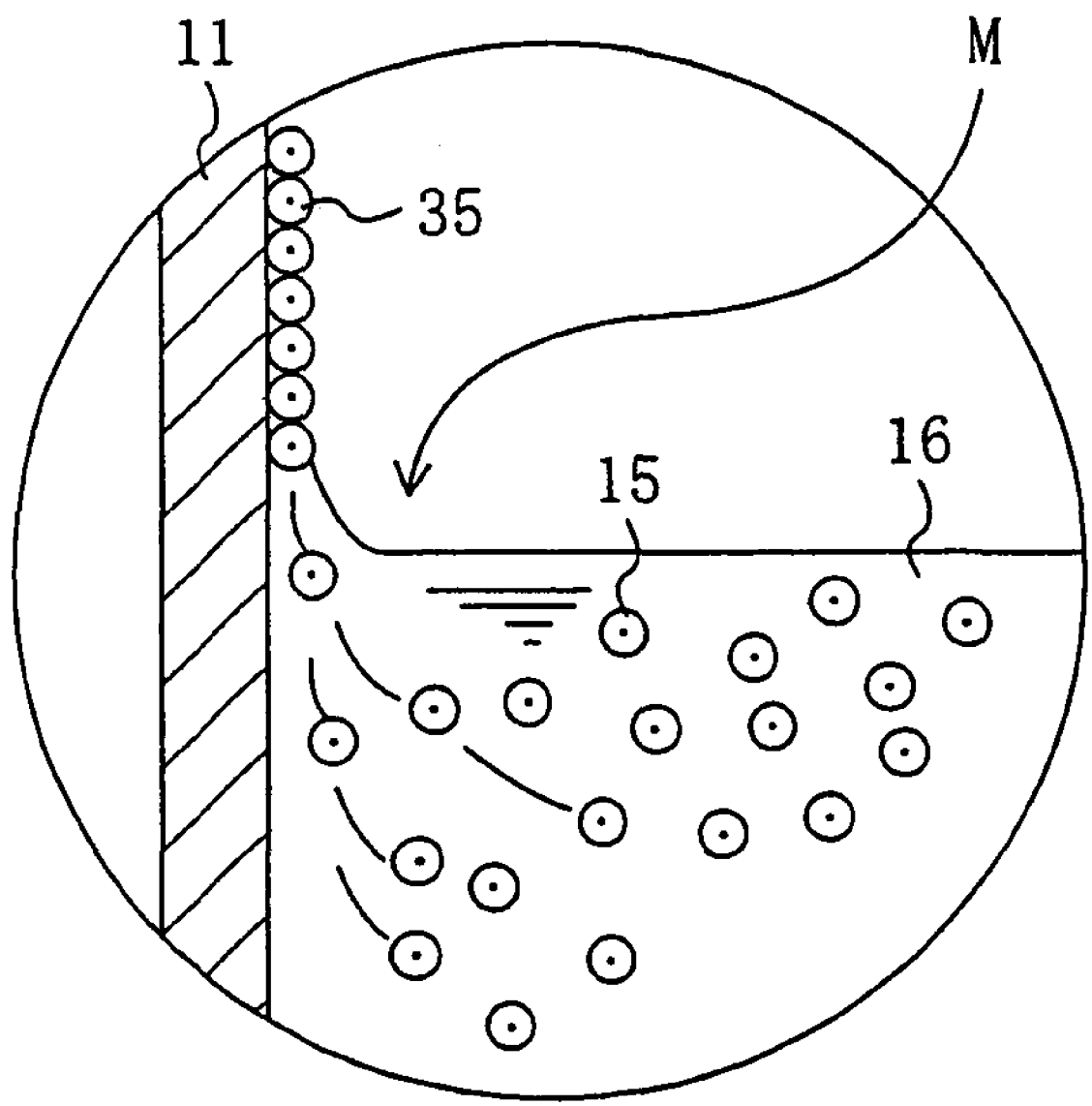
FIG. 9 is an enlarged view of a circled portion C in FIG. 6.

Method 5 in Embodiment 1 will be described in more detail with reference to FIGS. 6 and 9. FIG. 9 is an enlarged view of the circled portion C in FIG. 6.

First, the container 29 containing the liquid 16 is prepared. As described in Embodiment 1, the liquid 16 is a mixture of a phosphoric acid buffer solution, pH 5.3, having a concentration of 40 mM and a sodium chloride aqueous solution having a concentration of 40 mM in equal proportions, with the complex particles 15 dispersed therein.

The substrate 11 is then prepared, and, as shown in FIG. 6, put in the container 29 so that the surface of the substrate 11 stands vertical to the level of the liquid 16.

The level of the liquid 16 is then lowered or raised. In Embodiment 1 above, the liquid level was lowered. This process of lowering the level of the liquid 16 will be described in detail.

As the level of the liquid 16 is gradually lowered, the liquid level slightly rises along the substrate 11 at the interface between the liquid 16 containing the complex particles 15 and the substrate 11 as shown in FIG. 9, forming a meniscus portion M. In the meniscus portion M that has a large surface area, a dispersion medium (water in this embodiment) of the liquid 16 evaporates, resulting in reduction of the amount of the dispersion medium. This causes an effect similar to the micro-capillary effect in the meniscus portion M, where the liquid 16 flows toward this portion. As a result, the complex particles 15 exist in a significantly high concentration in the meniscus portion M of the liquid 16 and thus are arranged on the surface of the substrate 11 at high density with high precision. That is, a wet film 35 including the complex particles 15 arranged at high density with high precision is formed on the surface of the substrate 11. The meniscus portion M is also formed when the level of the liquid 16 is raised, and a wet film 35 including the complex particles 15 arranged at high density with high precision is formed on the surface of the substrate 11.

In the above process, as the time given for the arrangement of the complex particles 15 is longer, the complex particles 15 can be arranged at higher density with higher precision. It is therefore desirable to control the humidity at and around the liquid level so that the evaporation rate of the dispersion medium is low. For example, the process in this embodiment may be performed in a closed system, and an air conditioner or the like may be provided to control the humidity inside the closed system so that the dispersion medium can be gradually evaporated.

During the gradual lowering or raising of the level of the liquid 16, any vibration should desirably be eliminated to prevent the liquid level from being influenced by the vibration. For example, as a measure against vibration, the method in this embodiment may be performed on a vibration isolation base.

Figure 10:
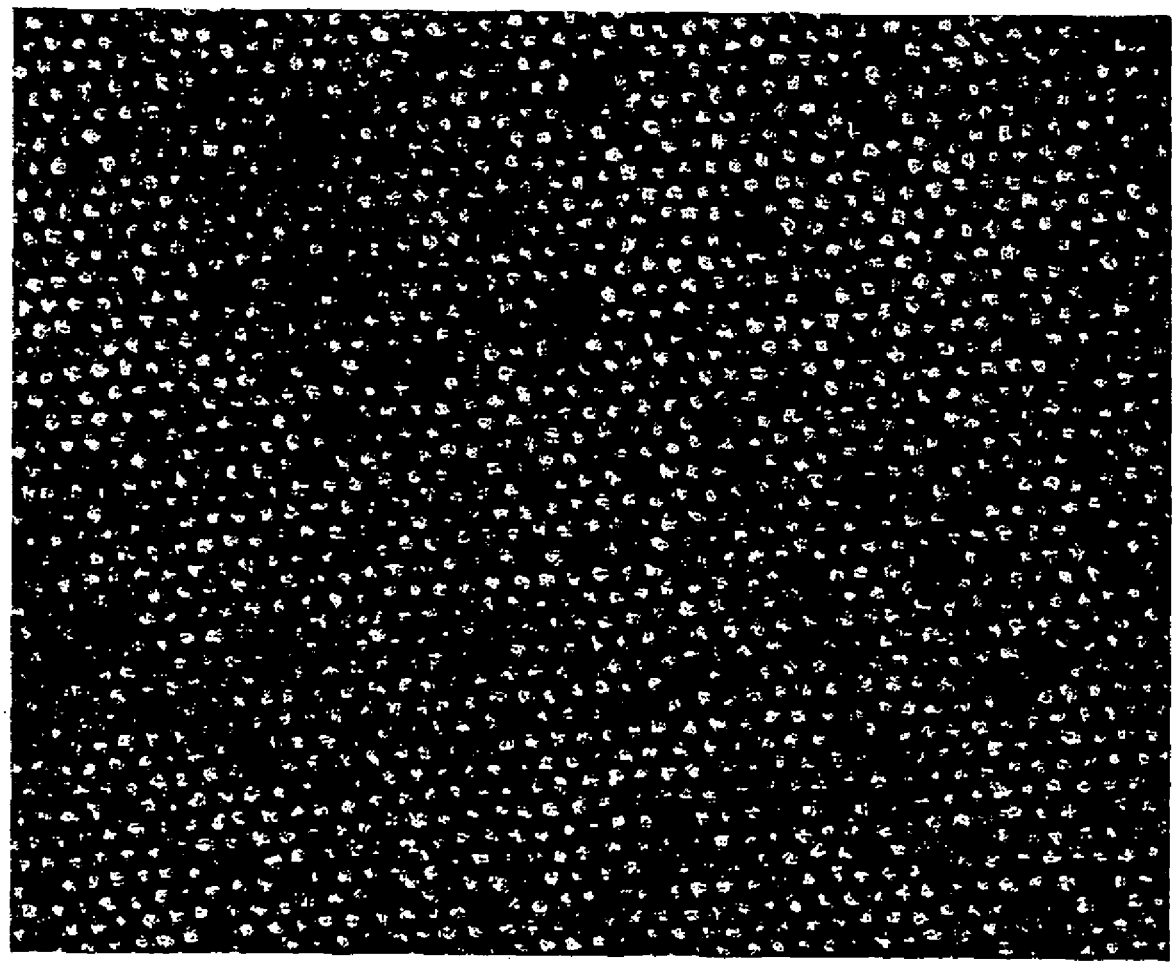
FIG. 10 is a photomicrograph of a particulate film of protein ferritin formed on a substrate surface.

By the process described above, the wet film 35 is formed on both surfaces of the substrate 11. Although the wet film 35 includes the complex particles 15 arranged two-dimensionally at high density with high precision, it is not completely free from the dispersion medium. The wet film 35 is therefore completely dried to obtain the substrate 11 with two-dimensional crystal of the complex particles 15 formed thereon. FIG. 10 is a photomicrograph of a two-dimensional crystal film of the complex particles 15 formed on the surfaces of the substrate 11 of this embodiment. In this method, the complex particles 15 are crystallized while being aligned in parallel with the liquid level. When the resultant two-dimensional crystal film is assumed to be in the (0001) face of a dense hexagonal lattice, the arrangement orientation is such that the direction vertical to the start line of the growth of the two-dimensional crystal film, that is, the growth direction is in the <1-100> direction. This indicates that the complex particles 15 can be arranged regularly at high density with high precision.

In the two-dimensional crystal film obtained by this method, since the arrangement orientation of the complex particles 15 is in order, the number of the complex particles 15 placed on the surface of the substrate 11 can be easily calculated. In other words, the number of the complex particles 15 placed on the surface of the substrate 11 can be easily controlled by changing the area of the substrate 11.

The level of the liquid 16 can be gradually lowered by forming a hole through the bottom of the container 29 to allow the liquid to drip through this hole, for example. The level of the liquid 16 may be raised by gradually increasing the liquid 16 in the container 29 utilizing siphonage, for example. In either case, the liquid level lowering or raising rate is preferably kept constant. Also, in general, the liquid level lowering or raising rate is preferably lower to ensure formation of a good film of the complex particles on the substrate 11. In particular, the liquid level lowering or raising rate for the liquid 16 is preferably 10 mm/min. or less. No specific lower limit is defined, but to achieve good economy industrially, it is appropriate to set the liquid level lowering or raising rate at about 0.1 mm/min. Thus, the liquid level lowering or raising rate is preferably about 0.1 to about 1 mm/min., more preferably about 0.12 to about 0.24 mm/min.

To lower the liquid level in this method, the liquid 16 may be drawn out by sucking the liquid 16 from above the container 29 via a tube having one open end positioned inside the container 29 near the bottom thereof and the other open end coupled to a suction means located outside the container 29, or by allowing the liquid to drop by gravity via a hole formed through the bottom of the container 29.

An arbitrary means may be taken to draw out the liquid 16. For example, a tube 30 may be used as shown in FIG. 6. One open end 37 of the tube 30 is positioned inside the container 29 near the bottom thereof and the other open end is coupled to a suction means (a syringe, an aspirator, a suction pump, or the like) located outside the container 29. By operating the suction means, the liquid 16 in the container 29 is sucked at the open end 37 of the tube positioned near the bottom of the container 29 upward through the tube to be drawn out from the container 29.

The open end 37 of the tube 30 positioned near the bottom of the container 29 is not specifically restricted in shape and structure. The open end may be a circular shape or an obliquely cut shape. Alternatively, a rectangular parallelepiped structure of which the bottom is open may be attached to the open end (see FIG. 11(a)), or the open end may have a funnel-shaped structure widened downwardly of which the bottom is open (see FIG. 11(b)).

Figure 11A:
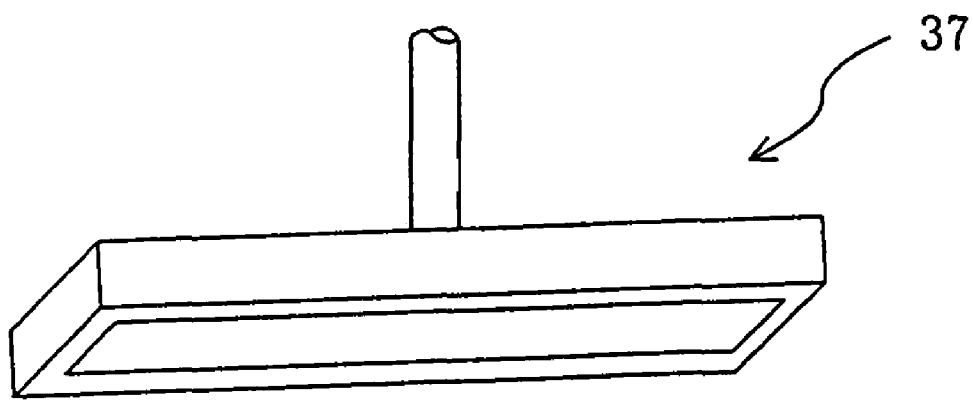
FIG. 11 illustrates examples of the shape and structure of an open end of a tube used in the present invention.
Figure 11B:
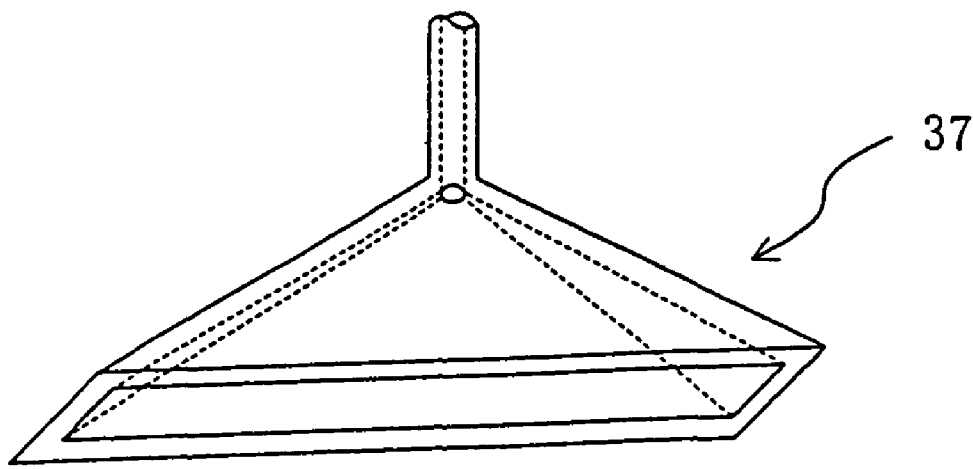
Figure 12A:
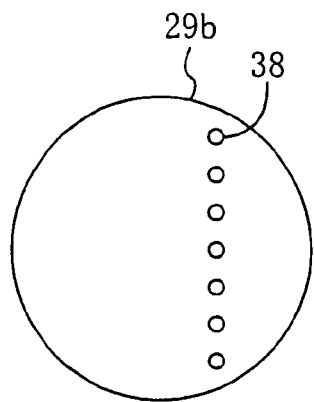
FIG. 12 illustrates examples of holes formed through the bottom of a container used in the present invention.
Figure 12B:
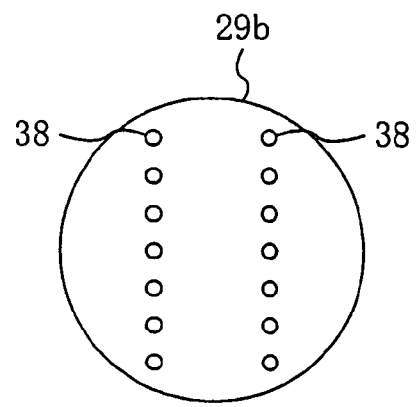
Figure 12C:
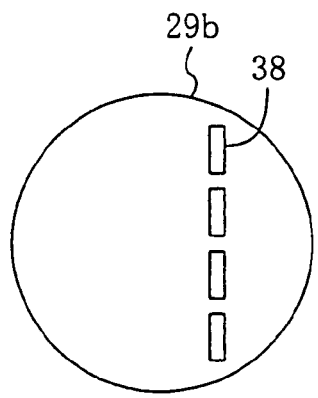
Figure 12D:
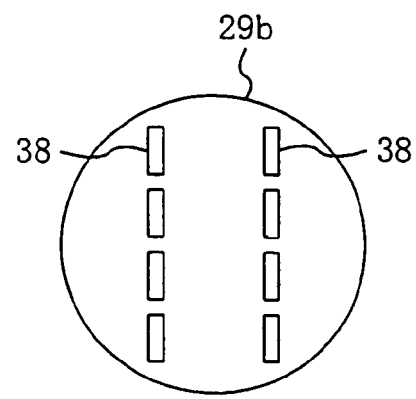
Figure 12E:
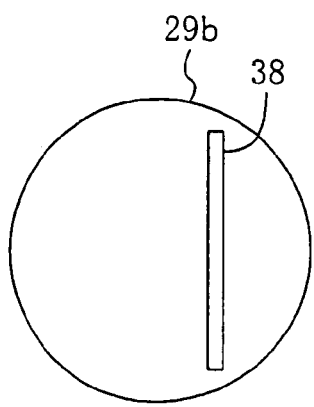
Figure 12F:
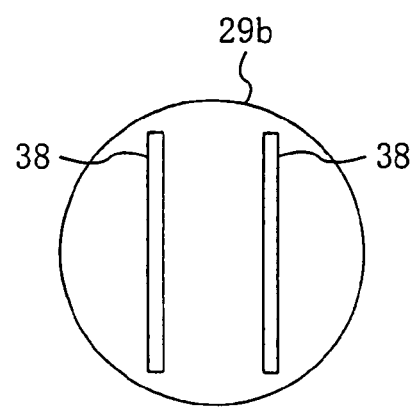

When the open end 37 of the tube 30 has the rectangular parallelepiped structure or the funnel-shaped structure as shown in FIG. 11(a) or 11(b), the tube 30 is preferably positioned so that the bottom of the rectangular parallelepiped structure or the funnel-shaped structure is in parallel with the bottom of the container 29.

When the liquid is drawn out by suction as described above, any disturbance of flow of the liquid 16 occurring near the substrate 11 may influence the formation of the film of the complex particles 15 (growth of the two-dimensional crystal film) on the surface of the substrate 11. Therefore, the substrate 11 is preferably placed at a position sufficiently apart from the open end of the tube positioned near the bottom of the container 29 (the opening of the rectangular parallelepiped structure or the funnel-shaped structure if such a structure is provided at the end of the tube), that is, at a position free from influence of disturbance of the flow of the liquid 16 caused by suction of the liquid 16.

In this method, the liquid 16 may be drawn out by dropping the liquid via a hole formed through the bottom of the container 29 by gravity, in place of sucking from above the container 29. Specifically, using a container 29 provided with a hole that enables the liquid 16 to flow (drop) therethrough by gravity at a flowing (dropping) rate equal to the liquid level lowering rate described above, the liquid 16 is drawn out from the bottom of the container 29.

When the liquid is drawn out by gravity as described above, only one hole 38 may be formed through the bottom of the container 29, or a plurality of holes 38 may be formed, as shown in FIG. 12. The hole 38 may have a circular shape, or a triangular or other polygonal shape (hereinafter, collectively called a polygonal shape). It may also be a slit. Such a slit-shaped hole 38 may be long or short. When a plurality of holes 38 in a circular, polygonal, or short-slit shape are formed through the bottom of the container 29, the plurality of holes 38 are preferably arranged in a line as shown in FIGS. 12(a) and 12(b), or they may be arranged in parallel lines as shown in FIGS. 12(c) and 12(d). In the case of forming a plurality of long slit-shaped holes 38 through the bottom of the container 29, they may be arranged in parallel with each other as shown in FIG. 12(f).

The plurality of holes 38 formed through the bottom of the container 29 are preferably lined in parallel with the surface of the substrate 11. In other words, the substrate 11 is preferably placed so that the surface of the substrate 11 is positioned in parallel with the plurality of holes 38 formed through the bottom of the container 29.

In the case described above where the liquid is drawn out by gravity, also, any disturbance of flow of the liquid 16 occurring near the substrate 11 may influence the formation of the film of the complex particles 15 (growth of the two-dimensional crystal film) on the surface of the substrate 11. Therefore, the substrate 11 is preferably placed at a position sufficiently apart from the portion where the holes are formed, that is, at a position free from influence of disturbance of the flow of the liquid 16 caused by the drawing of the liquid 16.

Figure 13:
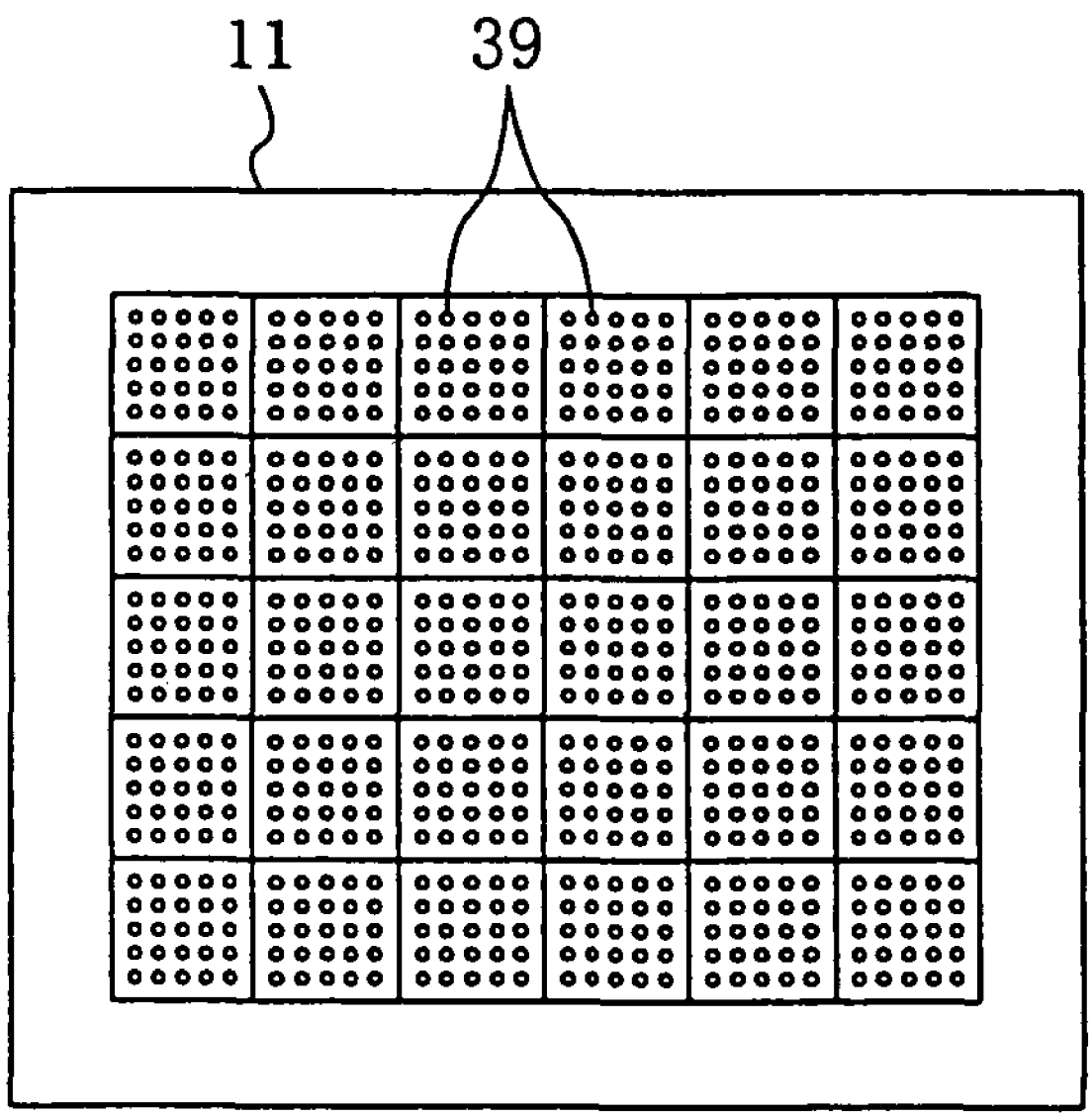
FIG. 13 is a view of a substrate having protrusions on a surface used in the present invention.
Figure 14A:
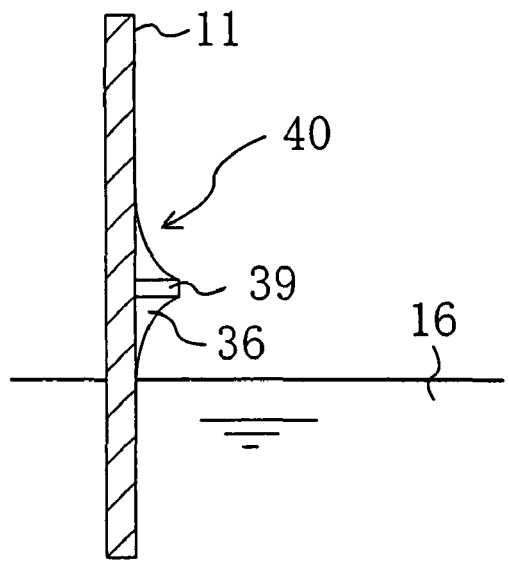
FIG. 14 illustrates a function of the protrusions formed on the substrate.
Figure 14B:
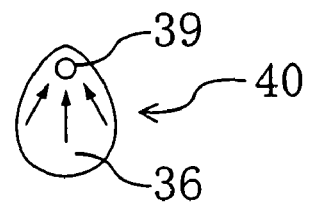
Figure 14C:
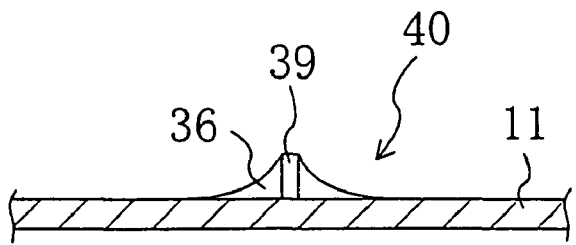

In this method, as shown in FIG. 13, the substrate 11 may have protrusions 39 on the surface thereof. As shown in FIGS. 14(a) to 14(c), by forming the protrusions 39 on the surface of the substrate 11, a larger amount of the liquid 16 is left behind on a portion 40 surrounding each protrusion 39 by the surface tension of the liquid 16. Therefore, a comparatively large number of complex particles 15 tend to gather on the surrounding portion 40. As a result, a multi-layer film of complex particles 15 can be selectively formed on the portion 40 surrounding the protrusion 39. In short, by forming the protrusions 39 on the surface of the substrate 11, it is possible to form a film of complex particles 15 arranged at higher density with higher precision.

For example, by using a substrate having a number of protrusions 39 formed on the surface in a matrix pattern, it is possible to form a film made of complex particles 15 arranged in layers at high density with high precision.

In addition, when the protrusions 39 are electrodes, the complex particles 15 are ferritin particles containing particles of an inorganic material such as iron inside, and the substrate 11 is a semiconductor substrate, for example, a ferritin film is formed on the semiconductor substrate. By removing the protein moiety of the ferritin by heat treatment or the like, only the particles of an inorganic material such as gold and iron are left behind on the semiconductor substrate. By using the thus-produced semiconductor substrate with a film made of the inorganic particles formed thereon, super-fine electronic devices such as transistors and diodes can be produced.

The formation of the protrusions 39 is not restricted to that shown in FIG. 13. Only one protrusion may be formed on the surface of the substrate 11, or a plurality of protrusions may be formed at random. Alternatively, a plurality of protrusions 39 may be placed regularly in a pattern other than the matrix pattern shown in FIG. 13.

In method 5 in Embodiment 1, the liquid 16 (a mixture of a phosphoric acid buffer solution, pH 5.3, having a concentration of 40 mM and a sodium chloride aqueous solution having a concentration of 40 mM in equal proportions, with the complex particles 15 dispersed therein) was used. This method is not restricted to this. For example, this method is greatly usable for production of a particulate film using particulates other than the complex particles 15.

For example, particles of inorganic materials and organic materials having a diameter of 50 nm or less are usable as the particulates in this method. Examples of the organic materials include synthetic polymers and proteins. Examples of the proteins include (1) virus proteins forming capsids or envelopes of viruses (for example, adenovirus, rotavirus, poliovirus, HK97, CCMV, and the like), (2) proteins belonging to the ferritin family such as ferritin and apoferritin, and (3) Dps proteins and MrgA proteins (refer to the protein data banks).

In this method, especially preferable are particles of the ferritin family such as ferritin and apoferritin having a diameter of 10 to 12 nm, or viruses, Dps proteins (protein particles one size smaller than ferritin particles having a diameter of about 9 nm and a core diameter of about 4 nm), and MrgA proteins having a diameter of 9 nm or less.

It is preferable to use protein particles obtained by translating DNAs or RNAs having the same base sequence. A plurality of protein particles obtained by translating the same DNA or RNA have completely the same structure and are not likely to have diameters varying every molecule. Moreover, protein particles have the self-assembling ability where they can construct a high-order structure together by recognizing one another. The protein particles having this ability can be arranged at high density with high precision.

Hereinafter, described is a case in which protein particles obtained by translating the same DNA are used as particulates in place of the complex particles 15, and a protein suspension with the protein particles suspended therein is used as the liquid 16.

In use of the protein suspension described above, if the concentration of the protein particles in the suspension is excessively low, the protein particles can exert only insufficient self-assembling function, failing to provide a good particulate film (two-dimensional crystal film). On the contrary, if the concentration is excessively high, the self-assembling function saturates. This is not only uneconomical, but also may possibly lead to layered arrangement of protein particles, resulting in formation of a locally threedimensional crystal film and thus failing to provide a film that can be effectively used industrially. In view of these, in this method, when a suspension containing ferritin particles is used as the liquid 16, for example, the protein concentration is in the range of 10 μg/ml to 500 mg/ml, preferably in the range of 10 μg/ml to 200 mg/ml, more preferably in the range of 0.5 mg/ml to 100 mg/ml.

In this method, the protein suspension may contain only protein in a dispersion medium (generally, pure water), or may additionally contain an electrolytic substance. The suspension containing only protein in pure water may generate large electrostatic repulsion between the substrate 11 and the protein particles, and this may cause slow adsorption of the protein particles to the substrate 11. To avoid this occurrence and accelerate formation of a film made of the protein particles, an electrolytic substance is added in this method. Examples of the electrolytic substance include sodium chloride, potassium chloride, calcium chloride, and magnesium chloride. If the content of the electrolytic substance is excessively large, the electrolytic substance is precipitated. In view of this, the content is suitably 300 mM or less, preferably about 150 mM (this is roughly the concentration of a normal saline solution), more preferably about 50 mM, in the case of sodium chloride.

Alternatively, the protein suspension may be heated to accelerate the formation of the particulate film made of the protein particles. During the heating of the protein suspension, however, convection is generated in the protein suspension. This may adversely affect the array of the protein particles and thus block the formation of the film of particulates arranged beautifully at high density with high precision. Therefore, when the protein suspension is heated to accelerate the formation of the particulate film, it is desirable to heat the suspension, the substrate, and all of the other components in uniform so that the particulate film can be formed in the equilibrium state blocking generation of convection of the protein suspension.

As another accelerating means, the surface of the substrate 11 may be subjected to hydrophilic treatment to charge the surface. Examples of the hydrophilic treatment of the surface of the substrate 11 include active ozone treatment under ultraviolet irradiation at high temperature (about 110° C.), oxygen plasma treatment, and amino silane treatment.

As yet another accelerating means, the pH of the protein suspension may be adjusted to fall within the range in which the charge of the substrate 11 immersed in the protein suspension is the opposite to the charge of the protein particles adsorbed to the surface of the substrate 11.

For example, the charge of the substrate subjected to amino silane hydrophilic treatment is plus when the pH is 11 or less, while the charge of the ferritin particles is minus when the pH is 5 or more. Therefore, if the pH of the ferritin suspension is adjusted to fall within the range of 5 to 11, it is possible to facilitate the adsorption of the ferritin particles to the substrate subjected to amino silane hydrophilic treatment (formation of the ferritin particle film on the substrate). In other words, the adsorption of the ferritin particles to the substrate subjected to amino silane hydrophilic treatment is facilitated by use of the attraction between the plus charge and the minus charge. Only specific regions of the substrate surface may be subjected to hydrophilic treatment to form the wet film 35 according to the pattern of the regions.

The substrate 11 is not necessarily subjected to hydrophilic treatment as described above, but may preferably be subjected to hydrophobic treatment depending on the type of the liquid 16. That is, depending on the type of the liquid 16 (or the dispersion medium), the wet film 35 can be formed only on a hydrophilic substrate surface or only on a hydrophobic substrate surface. For example, when a hydrophobic dispersion medium is used, the wet film 35 is formed only on a hydrophobic substrate surface, not a hydrophilic substrate surface. Exceptionally, in the case of protein, the substrate 11 is usable even when the surface thereof is hydrophobic in some cases. This is because protein is denatured on the surface of the substrate 11 and by this denaturation the surface of the substrate 11 becomes hydrophilic, to allow the wet film 35 to be formed on the hydrophilic surface.

EXAMPLES

Example 1

On a surface of a silicon substrate subjected to hydrophilic treatment with active ozone under ultraviolet irradiation at 110° C., apoferritin particles containing gold particles inside were arranged two-dimensionally at high density with high precision as shown in FIG. 2(a) by method 5 described above. For this process, used was a liquid containing gold particle-containing apoferritin in a normal saline solution in a concentration of 50 mg/ml. The liquid was drawn out from a container containing the liquid with a syringe at a drawing rate (liquid level lowering rate) of 0.1 mm/min.

The thus-produced substrate was heat-treated in a nitrogen gas atmosphere at 450° C. for one hour, to remove the apoferritin as the protein moiety and thus attain a substrate with only gold particles placed thereon in the shape of dots two-dimensionally at high density with high precision.

The resultant substrate was then put in contact with a thiol DNA aqueous solution, to attain a DNA sensor having one-to-one bonding of thiol DNAs to the gold particles. As the thiol DNA aqueous solution, used was an aqueous solution containing thiol DNAs in a concentration of 70 mg/ml warmed to 37° C. T4 phage DNAs were used as the DNAs and sulfur atoms were bonded to ends of the DNAs. The substrate was kept in contact with the thiol DNA aqueous solution for one hour.

Using the resultant DNA sensor, detection tests were conducted for the T4 phage DNA and M13 phage DNA unrelated at all to the T4 phage DNA. In the detection test for the T4 phage DNA, the DNA sensor exhibited high fluorescence intensity stably compared with the conventional DNA sensor, and thus detection was very easy. On the contrary, in the detection test for the M13 phage DNA, only background fluorescence intensity was detected, indicating that no hybridized DNA existed.

The DNA sensor used for the detection test for the T4 phage DNA was immersed in 100° C. pure water for 10 minutes, and then the surface of the DNA sensor having the hybridized DNA was exposed to flow of 100° C. pure water for 10 minutes. The resultant surface of the DNA sensor was measured for fluorescence and found to have the same fluorescence intensity as that of the background. From this result, it was confirmed that the hybridized DNA had dissociated from the thiol DNAs of the DNA sensor.

Using the resultant DNA sensor, a detection test for T4 phage DNA was performed again. As a result, the fluorescence intensity increased, and therefore, it was confirmed that the detection of DNA and the dissociation of hybridized DNA could be repeated a plurality of times.

Example 2

An RNA sensor was produced in the same manner as that described in Example 1, except that thiol RNAs (thiol RNAs produced using mRNAs obtained by transcription of T4 phages with sulfur atoms bonded to ends of the mRNAs) was used in place of the thiol DNA.

Using the resultant RNA sensor, a detection test was performed for separately synthesized complementary RNA. As a result, high fluorescence intensity was exhibited stably, and thus detection was very easy.

Example 3

First, as in Example 1, gold particles were placed two-dimensionally on a silicon substrate. A resin resist film made of polymthyl methacrylate (PMMA) was then formed on the substrate, and a photomask having openings was formed on the resin resist film.

Subsequently, the substrate was irradiated with light from above of the photomask, and then treated with a developer to pattern the resin resist film, to thereby expose part of the gold particles on the substrate.

Thereafter, thiol DNAs were bonded to the gold particles on the substrate.

The above operation was repeated while the type of the thiol DNAs (in base sequence or the like) to be bonded to the exposed gold particles was changed one after another, to attain a multi-type DNA sensor with DNAs having a number of different sequences bonded to the substrate. As the thiol DNAs, T4 phage DNAs were used, and sulfur atoms were bonded to ends of the DNAs. A solution containing such thiol DNAs in a concentration of 70 mg/ml and warmed to 37° C. was used. The substrate was kept in contact with the thiol DNA solution for one hour.

Using the thus-produced multi-type DNA sensor, detection tests were performed using a plurality of types of DNAs having different base sequences derived from T4 phage and a plurality of types of DNAs having different base sequences derived from M13 phage.

As a result, fluorescence was observed in expected sections in the detection test for the plurality of types of DNAs having different base sequences derived from T4 phage. The multi-type DNA sensor exhibited high fluorescence intensity stably compared with the conventional multi-type DNA sensor, and thus detection was very easy. On the contrary, in the detection test for the plurality of types of DNAs having different base sequences derived from M13 phage, only the background fluorescence intensity was detected, indicating that no hybridized DNA existed.

Example 4

A multi-type RNA sensor was produced in the same manner as that described in Example 3, except that thiol RNAs having a number of different sequences (thiol RNAs produced using part of T4 phage base sequences with sulfur atoms bonded to ends of the sequences) were used in place of the thiol DNAs having a number of different sequences.

Using the resultant multi-type RNA sensor, detection tests were performed using a plurality of mRNA sequences derived from T4 phage and a plurality of mRNA sequences derived from M13 phage. As a result, the multi-type RNA sensor exhibited high fluorescence intensity stably in expected sections, compared with the conventional multi-type RNA sensor, in the detection test for the T4 phage-derived mRNAs, and thus detection was very easy. On the contrary, in the detection test for the M13 phage-derived mRNAs, only the background fluorescence intensity was detected, indicating that no hybridized mRNA existed.

Example 5

First, a metal mask having openings was placed on a surface of a silicon substrate, and chromium and gold thin films were deposited by sputtering to form electrodes on the surface of the silicon substrate.

Gold particles were then placed as in Example 1 on the electrodes.

A positive potential was applied to an electrode in a region in which DNAs having a specific sequence were to be placed, and a negative potential was applied to the other electrodes. While applying these potentials, the substrate was put in contact with a thiol DNA solution, to allow thiol DNAs to establish one-to-one bonding to gold particles on the electrode.

The above operation was repeated while the type of the thiol DNAs (in base sequence or the like) was changed one after another and also the electrode to which the positive potential was applied was sequentially changed, to attain a multi-type DNA sensor with thiol DNAs having a number of different sequences bonded to the substrate.

As the types of thiol DNAs, those described in Embodiment 3 were used.

Using the thus-produced multi-type DNA sensor, detection tests as described in Example 3 were conducted, and substantially the same results as those described in Example 3 were obtained.

Example 6

A multi-type RNA sensor was produced in the same manner as that described in Example 5, except that thiol RNAs having a number of different sequences (thiol RNAs produced using part of T4 phage base sequences with sulfur atoms bonded to ends of the sequences) were used in place of the thiol DNAs having a number of different sequences.

As the types of thiol RNAs, those described in Embodiment 4 were used.

Using the thus-produced multi-type RNA sensor, detection tests as described in Example 4 were performed, and substantially the same results as those described in Example 4 were obtained.

Hereinafter, examples of production of a particulate film will be described.

Example 7

First, prepared was a ferritin suspension containing ferritin as particulates (containing ferritin particles having a size of 12 nm derived from a horse spleen in a normal saline solution in a concentration of 100 mg/ml). As the substrate, prepared was a silicon substrate (with a surface subjected to hydrophilic treatment with oxygen plasma) having a size of 40 mm wide×50 mm long×500 µm thick.

The silicon substrate was put in a container containing the ferritin suspension so as to stand vertical to the liquid level of the ferritin suspension. A tube (diameter: 1 mm) was placed in the container so that one open end thereof was positioned near the bottom of the container inside the container and the other open end was coupled to a syringe. The ferritin suspension was gradually drawn out from above the container at a liquid level lowering rate of 0.12 mm/min.

To prevent the substrate from being influenced by disturbance of the ferritin suspension generated due to the suction, the tube was placed so that the open end positioned near the bottom of the container was 20 mm apart from the silicon substrate.

By the above operation, a wet film was formed on both surfaces of the silicon substrate. By drying the wet film, attained was a substrate on both surfaces of which a particulate film made of ferritin particles arranged two-dimensionally at high density with high precision was formed.

Example 8

A particulate film was produced in the same manner as that described in Example 7, except that a container (10 cm×10 cm×10 cm, capacity: 1 liter) having one circular hole (diameter: 2 mm) formed through the bottom was used, in place of the syringe, so that the ferritin suspension in the container was dropped through this hole by gravity. As a result, in the particulate film, ferritin particles were arranged two-dimensionally on both surfaces of the silicon substrate at high density with high precision.

Example 9

A ferritin particle film was produced on both surfaces of the substrate 3 in the same manner as that described in Example 1, except that a plurality of protrusions (each protrusion has a lattice shape and part of the lattice has been circularly stamped) were formed on one surface of the silicon substrate (the size and surface treatment were the same as those in Example 1). This example will be described with reference to FIG. 14.

As the liquid level of the ferritin suspension 16 is lowered by suction with the syringe, the wet film 36 is formed on the portion 40 surrounding the protrusion 39 on the surface of the silicon substrate 11. The wet film 36 has a divergent drop-like shape widening downwardly toward the silicon substrate as shown in FIG. 14(b). The ferritin particles of the wet film 36 gather toward the protrusion 39 as indicated by the arrows due to decrease in the amount of the dispersion medium of the wet film 36 and the micro-capillary effect. Therefore, the concentration of the ferritin particles increases along the gathering path toward the protrusion 39.

Thus, as shown in FIG. 14(c), the particulate film produced in this example with ferritin particles arranged two-dimensionally at high density with high precision has a thickness that is largest at a position adjacent to the protrusion 39 and gradually decreases as the position is farther from the protrusion 39.

Example 10

A particulate film was produced in the same manner as that described in Example 9, except that an apoferritin suspension with zinc oxide-containing apoferritin particles, in place of the ferritin particles, suspended therein was used.

The particulate film was heat-treated in a nitrogen atmosphere at 450° C. for two hours. As a result, the protein moiety was removed, and super-fine particles of zinc oxide were formed on the silicon substrate.

The air containing a trace amount of mercaptan was sprayed to the resultant substrate. As a result, the amount of mercaptan in the air was reduced.

The substrate was then irradiated with an electronic beam to measure fluorescence, and it was found that the fluores cence intensity was different between before and after the exposure to the air containing a trace amount of mercaptan. It was therefore confirmed that the substrate with the particulate film formed thereon in this example was effective as a microsensor.

As described above, according to the method for producing a particulate film of the present invention, it is possible to easily produce a two-dimensional crystal film made of particulates having a diameter of the order of nanometers arranged at high density and at desired positions with high precision.

Therefore, according to the method for producing a particulate film of the present invention, two-dimensional crystal films made of particulates can be easily mass-produced in the industrial scale.

INDUSTRIAL APPLICABILITY

The nucleotide detector of the present invention is usable for devices utilizing complementarity of nucleotides, such as DNA sensors and RNA sensors.

The method for producing a particulate film of the present invention is usable for fabrication of devices requiring super-fine patterns, in particular, for fabrication of diffraction gratings, nucleotide detectors, and super-fine electronic devices such as transistors and diodes.

The invention claimed is:

1. A method for manufacturing a nucleotide detector comprising the steps of:
   (a) arranging, on a substrate, complex particles each including a metal particle and a protein molecule holding the metal particle therein;
   (b) removing the protein molecules so that the metal particles are left on the substrate; and
   (c) bonding one of a pair of nucleotide molecules capable of conjugating with each other to each of the metal particles left on the substrate.

2. The method for manufacturing a nucleotide detector of claim 1,
   wherein the protein molecules are Dps protein or apoferritin.

3. The method for manufacturing a nucleotide detector of claim 1,
   wherein the nucleotide molecules comprise a plurality of types of nucleotide molecules having different base sequences.

4. The method for manufacturing a nucleotide detector of claim 1,
   wherein the one of the pair of nucleotide molecules has a sulfur atom at one end,
   the metal particles are made of gold, and
   the step (c) comprises a sub-step of:
   (c1) reacting the sulfur atom with the metal particles, thereby bonding the metal particles and the one of the pair of nucleotide molecules.

5. The method for manufacturing a nucleotide detector of claim 4,
   wherein the one of the pair of nucleotide molecules and the metal particles are reacted by bringing an aqueous solution including the one of the pair of nucleotide molecules having the sulfur atom at one end in contact with the substrate on which surface the metal particle is left.

6. The method for manufacturing a nucleotide detector of claim 5,
   wherein the step (c) is performed at a temperature between 20° C. and 60° C., inclusively.

7. The method for manufacturing a nucleotide detector of claim 5,
wherein the amount of the one of the pair of nucleotide molecules having the sulfur atom at one end included in the aqueous solution is more than the amount of the metal particles left on the substrate.

8. The method for manufacturing a nucleotide detector of claim 6,
wherein the protein molecule is an apoferritin having holes therein, and
the complex particles including the metal particles and the protein molecules holding the metal particles therein are obtained by the steps of:
substituting amino acid residues located within the apoferritin and positively charging the holes within the apoferritin; and
introducing $AuCl_4^{31}$ into the holes of that apoferritin.

9. The method for manufacturing a nucleotide detector of claim 1,
wherein the step (c) comprises sub-steps of:
(c2) forming a resist film, having a first opening exposing a portion of the metal particles left on the substrate, on the substrate; and
(c3) reacting the metal particles exposed in the first opening with the one of the pair of nucleotide molecules.

10. The method for manufacturing a nucleotide detector of claim 3,
wherein the step (c) comprises sub-steps of:
(c2) forming a resist film, having a first opening exposing a portion of the metal particles left on the substrate, on the substrate;
(c3) reacting the metal particles exposed in the first opening with the one of the pair of nucleotide molecules;
(c4) forming another resist film, having a second opening exposing a portion of the metal particles left on the substrate and provided in a different position as the first opening, on the substrate, after the sub-step (c3); and
(c5) reacting the metal particles exposed in the second opening with one of a pair of nucleotide molecules having a different base sequence as the one of the pair of nucleotide molecules used in step (c3).

11. The method for manufacturing a nucleotide detector of claim 1,
wherein the metal particles are made of gold,
a plurality of electrodes are interposed between the substrate and the metal particles, and
the step (c) comprises a sub-step of:
applying electric potentials to a first electrode while applying no electric potential to electrodes other than the first electrode, and bonding the one of the pair of nucleotide molecules having the sulfur atom at one end and the metal particles provided on the first electrode.

12. The method for manufacturing a nucleotide detector of claim 3,
wherein the one of the pair of nucleotide molecules has a sulfur atom at one end,
the metal particles are made of gold,
a plurality of electrodes are interposed between the substrate and the metal particles, and
the step (c) comprises sub-steps of:
(c6) applying electric potentials to a first electrode while applying no electric potential to electrodes other than the first electrode, and bonding the one of the sulfur atom and the metal particles provided on the first electrode; and
(c7) applying electric potentials to a second electrode while applying no electric potential to electrodes other than the second electrode, and bonding the sulfur atom and the metal particles provided on the second electrode.

* * * * *

UNITED STATES PATENT AND TRADEMARK OFFICE
CERTIFICATE OF CORRECTION

PATENT NO.       : 7,129,047 B2
APPLICATION NO.  : 10/628840
DATED            : October 31, 2006
INVENTOR(S)      : Ichiro Yamashita It is certified that error appears in the above-identified patent and that said Letters Patent is hereby corrected as shown below:

Column 23

Line 17, Claim 8, "AuCl431" should be -- $AuCl_4^-$ --
Line 23, Claim 9, delete second occurrence of "on the substrate"
Line 32, Claim 10, delete second occurrence of "on the substrate"

Signed and Sealed this

Twentieth Day of February, 2007

JON W. DUDAS
*Director of the United States Patent and Trademark Office*